US012514759B2

(12) United States Patent
Strong et al.

(10) Patent No.: US 12,514,759 B2
(45) Date of Patent: Jan. 6, 2026

(54) TAMPON WITH WICKING MEMBER AND IMPROVED MANUFACTURABILITY

(71) Applicant: The Procter & Gamble Company, Cincinnati, OH (US)

(72) Inventors: Kevin Charles Strong, Loveland, OH (US); Henry A. Brown, Cincinnati, OH (US); Evan Joseph Durling, West Chester, OH (US); Ryo Minoguchi, Cincinnati, OH (US); Khalid Qureshi, Mason, OH (US); Lymarie Semidey-Flecha, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 18/429,861

(22) Filed: Feb. 1, 2024

(65) Prior Publication Data

US 2024/0164952 A1 May 23, 2024

Related U.S. Application Data

(63) Continuation of application No. 16/716,553, filed on Dec. 17, 2019, now Pat. No. 11,925,535.

(Continued)

(51) Int. Cl.

| | |
|---|---|
| ***A61F 13/15*** | (2006.01) |
| ***A61F 13/20*** | (2006.01) |
| ***A61F 13/34*** | (2006.01) |

(52) U.S. Cl.

CPC .... *A61F 13/15203* (2013.01); *A61F 13/2054* (2013.01); *A61F 13/2074* (2013.01);

(Continued)

(58) Field of Classification Search

CPC ............ A61F 13/20–2097; A61F 13/34; A61F 2013/15487; Y10S 604/904

See application file for complete search history.

(56) References Cited

U.S. PATENT DOCUMENTS

| | | | |
|---|---|---|---|
| 1,932,383 | A | 10/1933 | Richardson |
| 2,123,750 | A | 7/1938 | Schulz |

(Continued)

FOREIGN PATENT DOCUMENTS

| | | | |
|---|---|---|---|
| CN | 1283979 | A | 2/2001 |
| CN | 1516569 | A | 7/2004 |

(Continued)

OTHER PUBLICATIONS

Gopalakrishnan, D. Spunbonded Nonwovens—An Overview. Feb. 2007, [online], [retrieved on Aug. 4, 2023]. Retrieved from the Internet <URL: https://www.fibre2fashion.com/industry-article/1575/spunbonded-nonwovens-an-overview> (Year: 2007).*

(Continued)

*Primary Examiner* — Nicholas J. Weiss
*Assistant Examiner* — Linnae E. Raymond
(74) *Attorney, Agent, or Firm* — Sarah M. DeCristofaro

(57) ABSTRACT

A tampon including a pledget, a wicking member disposed in direct contact with the pledget, and a withdrawal cord is disclosed. The wicking member is non-coaxially arranged with respect to the withdrawal cord.

23 Claims, 12 Drawing Sheets

Related U.S. Application Data

(60) Provisional application No. 62/857,977, filed on Jun. 6, 2019, provisional application No. 62/834,427, filed on Apr. 16, 2019, provisional application No. 62/780,388, filed on Dec. 17, 2018.

(52) U.S. Cl.
CPC ...... *A61F 13/2077* (2013.01); *A61F 13/2085* (2013.01); *A61F 13/34* (2013.01); *A61F 2013/15487* (2013.01)

(56) References Cited

U.S. PATENT DOCUMENTS

| | | | | |
|---|---|---|---|---|
| 2,391,343 | A | 12/1945 | Otto | |
| 2,412,391 | A | 12/1946 | Crockford | |
| 2,412,861 | A | 12/1946 | William | |
| 2,499,414 | A | 3/1950 | Rabell | |
| 3,397,695 | A | 8/1968 | Voss | |
| 3,731,687 | A | 5/1973 | Glassman | |
| 3,732,866 | A * | 5/1973 | Accavallo | A61F 13/206 604/377 |
| RE27,677 | E | 6/1973 | Glassman | |
| 3,811,445 | A | 5/1974 | Dostal | |
| 4,200,101 | A | 4/1980 | Glassman | |
| 4,318,407 | A | 3/1982 | Woon | |
| 4,335,720 | A | 6/1982 | Glassman | |
| 4,624,668 | A | 11/1986 | Siegers | |
| 4,835,042 | A | 5/1989 | Dohzono | |
| 5,891,123 | A | 4/1999 | Balzar | |
| 6,186,995 | B1 | 2/2001 | Tharpe, Jr. | |
| 6,258,074 | B1 | 7/2001 | Prazak | |
| 6,258,075 | B1 | 7/2001 | Taylor | |
| 6,315,763 | B1 * | 11/2001 | Albright | A61F 13/2051 604/385.18 |
| 6,840,927 | B2 * | 1/2005 | Hasse | A61F 13/208 604/385.18 |
| 7,799,966 | B2 | 9/2010 | Williams | |
| 8,827,974 | B2 | 9/2014 | Schmidt-forst | |
| 2001/0021839 | A1 | 9/2001 | Kashiwagi | |
| 2003/0097106 | A1 | 5/2003 | Hasse et al. | |
| 2003/0097108 | A1 * | 5/2003 | Hasse | A61F 13/208 604/385.18 |
| 2003/0097112 | A1 * | 5/2003 | Gilbert | A61F 13/2051 604/385.17 |
| 2004/0000193 | A1 | 1/2004 | Grotendorst | |
| 2004/0019317 | A1 | 1/2004 | Takagi | |
| 2005/0055003 | A1 * | 3/2005 | Bittner | A61F 13/2051 604/385.18 |
| 2005/0096619 | A1 | 5/2005 | Costa | |
| 2006/0025742 | A1 * | 2/2006 | Hasse | A61F 13/26 604/385.18 |
| 2007/0016156 | A1 | 1/2007 | Burgdorf et al. | |
| 2007/0260211 | A1 | 11/2007 | Schmidt-forst | |
| 2008/0132868 | A1 | 6/2008 | Jorgensen | |
| 2008/0262463 | A1 | 10/2008 | Noel et al. | |
| 2008/0275411 | A1 | 11/2008 | Hughes et al. | |
| 2009/0260205 | A1 | 10/2009 | Binner et al. | |
| 2010/0069866 | A1 | 3/2010 | Binner et al. | |
| 2010/0130953 | A1 | 5/2010 | Fung et al. | |
| 2010/0174262 | A1 * | 7/2010 | Watanabe | A61F 13/206 604/385.18 |
| 2010/0268182 | A1 | 10/2010 | Edgett | |
| 2012/0053550 | A1 * | 3/2012 | Kinoshita | A61F 13/51305 604/385.17 |
| 2012/0101462 | A1 | 4/2012 | Lee | |
| 2012/0277704 | A1 | 11/2012 | Marinelli | |
| 2013/0138071 | A1 | 5/2013 | Fung et al. | |
| 2013/0160259 | A1 | 6/2013 | Mcdaniel et al. | |
| 2015/0157511 | A1 * | 6/2015 | Strong | A61F 13/34 604/385.18 |
| 2015/0374558 | A1 | 12/2015 | Strong et al. | |
| 2018/0125724 | A1 | 5/2018 | Brown et al. | |
| 2020/0188186 | A1 | 6/2020 | Strong et al. | |
| 2020/0188189 | A1 | 6/2020 | Strong et al. | |
| 2020/0188190 | A1 | 6/2020 | Strong | |

FOREIGN PATENT DOCUMENTS

| | | | | |
|---|---|---|---|---|
| CN | 101874756 | A | 11/2010 | |
| WO | 0061052 | A1 | 10/2000 | |
| WO | 2000061052 | A1 | 10/2000 | |
| WO | 02058609 | A2 | 8/2002 | |
| WO | 02058614 | A1 | 8/2002 | |
| WO | WO-2005063161 | A1 * | 7/2005 | A61F 13/2051 |
| WO | 2005112861 | A1 | 12/2005 | |
| WO | 2007078413 | A1 | 7/2007 | |
| WO | 2016207242 | A1 | 12/2016 | |
| WO | WO-03022196 | A2 * | 3/2023 | A61F 13/15804 |

OTHER PUBLICATIONS

McLoughlin, J, and Mitchell, A. Textiles and Fashion. Cambridge: Woodhead Publishing, 2015, Ch. 16 pp. 379-411 [online], [ retrieved on Sep. 27, 2022]. Retrieved from the Internet: <URL: https://www.sciencedirect.com/science/article/pii/B9781845699314000167> (Year: 2015).*

Fiery Software. Delta E, Delta H, Delta T: What Does It Mean? [online], [retrieved on Aug. 4, 2023]. Retrieved from the Internet <URL : chrome-extension://efaidnbmnnnibpcajpcglclefindmkaj/https://help.fiery.com/fieryxf/KnowledgeBase/ColorManagement/Delta%20E_H_T.pdf> (Year: 2023).*

All Office Actions, U.S. Appl. No. 16/716,556.

All Office Actions, U.S. Appl. No. 16/716,553.

All Office Actions; U.S. Appl. No. 16/716,550, filed Dec. 17, 2019.

All Office Actions; U.S. Appl. No. 18/459,475, filed Sep. 1, 2023.

All Office Actions; U.S. Appl. No. 18/599,355, filed Mar. 8, 2024.

Fiery Software. Delta E, Delta H, Delta T: What Does It Mean?. Online retrieved from chrome extension://efaidnbmnn-nibpcajpcglclefindmkaj/https://help.fiery.com/fieryxf/KnowledgeBase/ColorManagement/Delta%20E_H_T.pdf, dated 2023, pp. 04.

Gopalakrishnan, "D. Spunbonded Nonwovens"—An Overview, Online retrieved from https://www.fibre2fashion.com/industry-article/1575/spunbonded-nonwovens-an-overview. Year: 2007, pp. 05.

International Search Report and Written Opinion; Application Ser. No. PCT/US2019/066696; dated Apr. 28, 2020, 15 pages.

Mcloughlin, J, and Mitchell, A.; "Textiles and Fashion, Materials design and technology", Cambridge: Woodhead Publishing, Retrieved from the Internet: URL:https://www.sciencedirect.com/science/article/pii/B9781845699314000167, Chapter 16, ISBN-978: 0-85709-561-9, Year 2015, pp. 379-411.

U.S. Appl. No. 18/459,475, filed Sep. 1, 2023, Kevin Charles Strong et al.

U.S. Appl. No. 18/599,355, filed Mar. 8, 2024, to Kevin Charles Strong.

All Office Actions; U.S. Appl. No. 18/748,285, filed Jun. 20, 2024.

U.S. Appl. No. 18/748,285, filed Jun. 20, 2024, Kevin Charles Strong et al.

* cited by examiner 31
11
12a 30
15a
15
15b
12
12b
100b
100a

TAMPON WITH WICKING MEMBER AND IMPROVED MANUFACTURABILITY

CROSS-REFERENCE TO RELATED APPLICATIONS

This application is a continuation of U.S. Nonprovisional application Ser. No. 16/716,553 filed Dec. 17, 2019, which claims the benefit of U.S. Provisional Application No. 62/857,977 filed Jun. 6, 2019, U.S. Provisional Application No. 62/834,427 857977 filed Apr. 16, 2019, and U.S. Provisional Application No. 62/780,388 filed Dec. 17, 2018, the entire disclosures of which are fully incorporated by reference herein.

BACKGROUND OF THE INVENTION

A variety of designs for absorbent tampons have been manufactured for a number of years, and used by women to capture and absorb menstrual fluid internally, in conjunction with, or as an alternative to, externally worn feminine hygiene pads. Many women prefer to use tampons as an alternative to feminine hygiene pads at least some of the time during menstruation, because, among other reasons, tampons are used internally and are thereby discrete, creating none of the bulk under clothing that is associated with many types of feminine hygiene pads.

Particularly when a feminine hygiene pad is not used in conjunction therewith, it is important that the tampon capture and absorb most if not substantially all of the menstrual fluid that is discharged during the tampon's usage duration (to the extent of its absorption capacity), to help avoid a leakage of fluid that may soil underwear, outer clothing, bedclothes, etc. The prior art has recognized various ways in which tampons might fail to perform effectively. One such way is sometimes referred to as "bypass" failure. Bypass failure occurs when the menstrual fluid travels along the length of the vaginal cavity without contacting the tampon, or the tampon, while having available absorption capacity, otherwise fails to capture and absorb the fluid.

A variety of approaches to tampon design have sought to mitigate such failure. One approach that has proven effective has been to include a wicking member as part of the withdrawal cord. The wicking member is a material/structure selected and configured to extend downward (or trail, to the rear of) the main pledget, along with the withdrawal cord, thereby extending further down the vaginal cavity toward the vaginal opening than the pledget, following insertion. Appropriately configured, the wicking member can engage menstrual fluid flowing along the vaginal cavity past the pledget, capture it, and wick it back to the pledget. Current approaches to manufacture of such tampons, however, have shown to be inefficient, and current selections of configurations and materials have shown to be less effective than may be fully realized.

Accordingly, there remains room for improvement in the construction and method of manufacture of tampons with wicking members.

DETAILED DESCRIPTION OF EXAMPLES

Definitions

Figure 1:
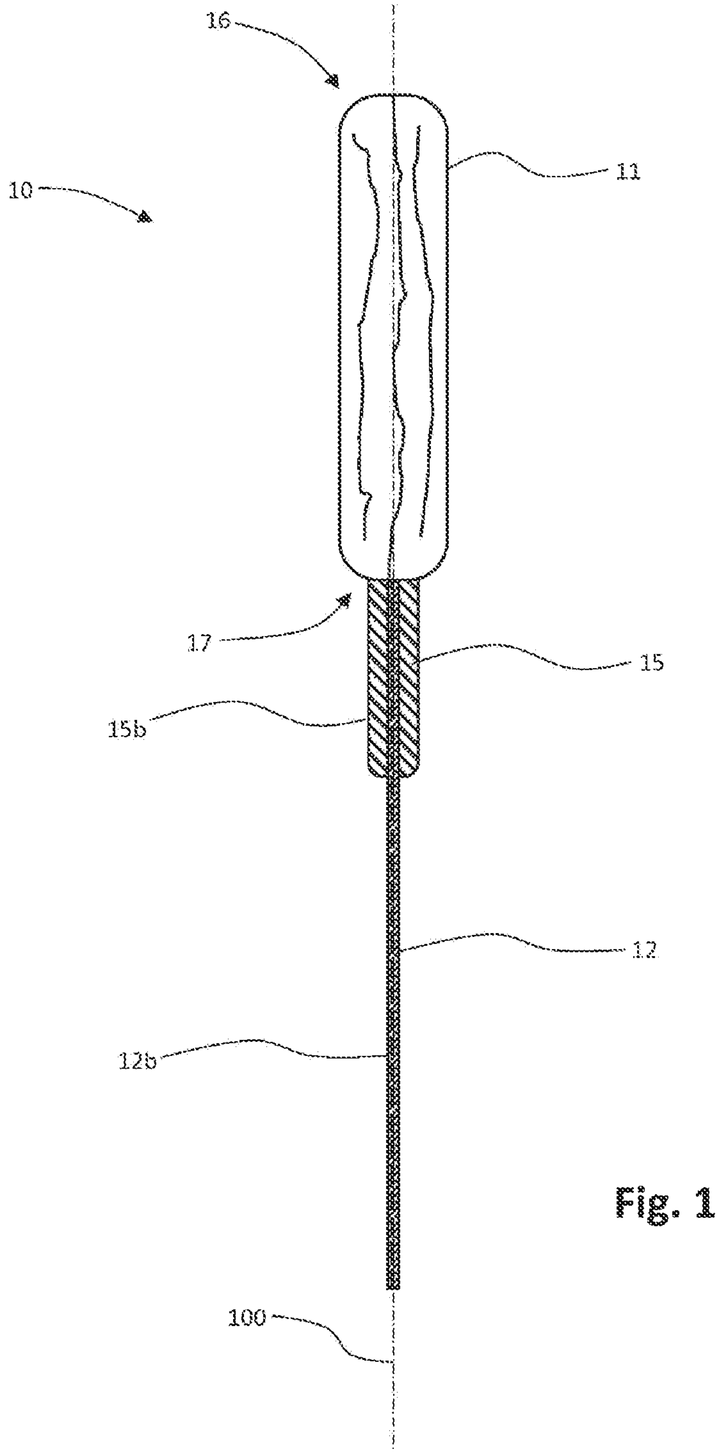
FIG. 1 is a longitudinal side view of an example of a tampon with a pledget shaped and compressed into a self-sustaining form.

As used herein the term "tampon" refers to any type of absorbent structure which is inserted into the vaginal canal for the absorption of fluid therefrom. Typically, a tampon includes a pledget structure including a quantity of absorbent material, often absorbent fibrous material, which pledget structure has been bunched, folded and/or compressed in one or more radial directions, the longitudinal direction, or both, via application of pressure, heat and moisture control, in order to provide a formed tampon having a size, shape and stability of form to facilitate insertion into the vagina. A tampon which has been so formed is referred to herein has a "self-sustaining" form. The degree of compression, heat and moisture control applied to the pledget is sufficient such that in the subsequent absence of the external forces and absence of substantial contact with moisture, the pledget will tend to retain its general formed shape and size.

It will be understood by persons of ordinary skill in the art that this self-sustaining form typically does not persist following insertion of the tampon. Once the tampon is inserted and begins to contact and absorb fluid, the pledget will swell with absorbed fluid, expand and lose its self-sustaining form.

As used herein the terms "pledget" or "tampon pledget" are intended to be interchangeable and refer to a structure including absorbent material configured to perform the primary function of the tampon, absorption of menstrual fluid. A tampon pledget is sometimes referred to as a tampon blank, or a softwind, and the term "pledget" is intended to include structures designated by such terms as well.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix, and is not intended to include the interlabial space, including the floor of the vestibule. The external features of the female genitalia generally are not included within the term "vaginal cavity" as used herein.

With respect to a tampon, the "longitudinal" direction is the ordinary general direction of ejection from an applicator; and also corresponds with the ordinary general direction of insertion into and withdrawal from the vaginal cavity in normal use. For a completely manufactured, pre-use tampon that has a pledget with a generally cylindrical or capsule-shaped self-sustaining form, the longitudinal axis of the form generally lies along the longitudinal direction. The "radial" or "lateral" direction is a direction perpendicular to the longitudinal direction. References to "length" herein refer to a dimension along the longitudinal direction; references to "width" herein refer to a dimension along the lateral direction.

"Withdrawal cord" refers to any section of string, yarn, cord, ribbon, strip material or other flexible/pliable elongate structure typically (although not necessarily) formed of fibrous material, attached to and/or extending from a tampon pledget and trailing from its rearward end. A withdrawal cord of sufficient length may be provided with a tampon for the purpose of providing a relatively thin and flexible trailing member of sufficient length to allow for a portion thereof to trail and remain outside of the introitus following full insertion of the tampon, which the user may easily grasp and pull to withdraw the tampon from her body following a desired duration of use.

The present disclosure relates to an improved absorbent tampon provided with a leakage protection feature. It has been found that there are several potential mechanisms beyond simple bypass flow which may contribute to tampon leakage. Without wishing to be bound by theory, some of these mechanisms may be explained by the following observations. It has been found that many current tampons show stains along the length of the withdrawal cord following use and withdrawal, associated with incidents of tampon leakage. It is believed that the withdrawal cord of many current tampons may offer an escape route for menstrual fluid present at the base of the vaginal cavity, by operating as a wicking mechanism.

During a tampon change, some residual menstrual fluid may be left in the vaginal cavity near the introitus. This may be fluid that was absorbed by the tampon being removed, but is subsequently expressed from the tampon as it is drawn out of the body through the relatively narrow sphincter of the vagina. Such residual fluid, particularly if located near the introitus (i.e. in the lower vaginal cavity) may not be effectively absorbed by the replacement tampon. This is particularly true of many current tampons which are typically inserted somewhat more deeply into the vaginal canal. These circumstances, as well as bypass leakage described above, and other leakage circumstances are addressed by tampons within contemplation of the present disclosure.

FIGS. 1, 2, 3A and 3B show one non-limiting example of such an absorbent tampon 10, having a longitudinal axis 100, a pledget 11 having a forward end 16 and a rearward end 17 and a withdrawal cord 12 attached to the pledget and having a leading portion 12*a* attached to the pledget and a trailing portion 12*b* extending rearward from a location proximate the rearward end 17. Tampons contemplated herein, however, are not limited to structures having the particular configuration shown in the drawings.

Figure 2:
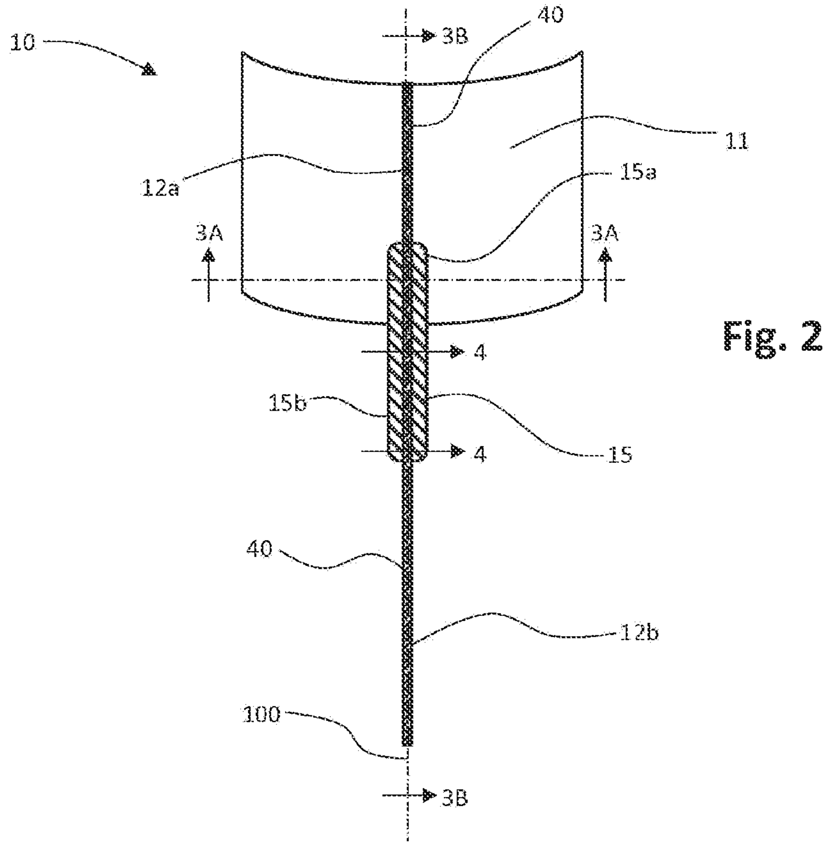
FIG. 2 is a longitudinal front side view of an example of a tampon before the pledget has been shaped and compressed into a self-sustaining form.
Figure 3A:
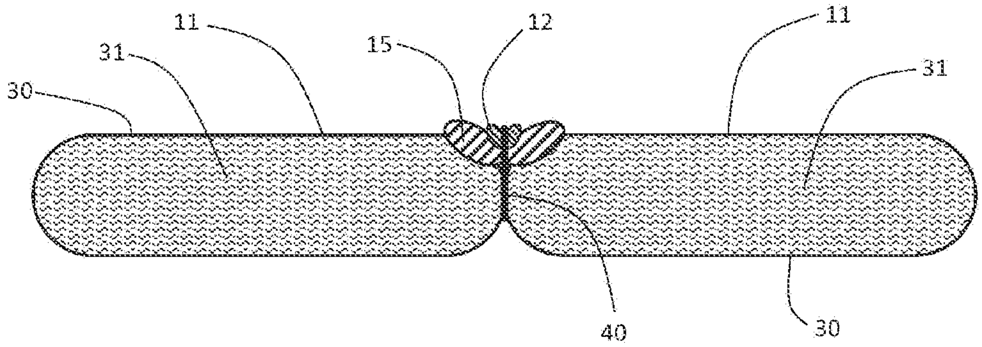
FIG. 3A is a lateral cross section of the tampon shown in FIG. 2, taken through line 3A-3A in FIG. 2.

The pledget 11 of the tampon 10 as shown in FIGS. 1 and 2 has a forward end 16 and a rearward end 17. During manufacture of the tampons the pledget 11 may be folded, bunched, compressed and/or otherwise formed in size and shape, from its initially manufactured configuration (e.g. as shown in FIGS. 2 and 3A) into a generally cylindrical configuration (e.g. as shown in FIG. 1) in the radial direction, the longitudinal direction, or in both the radial and longitudinal directions. While the pledget 11 may be formed into a substantially cylindrical configuration a suggested in FIG. 1, other shapes are also possible. These may include shapes having a cross section which may be described as oval, elliptical, ovoid, stadium, rectangular, triangular, trapezoidal, semi-circular, or other suitable shapes. FIGS. 5A-5E sequentially illustrate in lateral cross section, the manner in which a non-limiting example of pledget 11 having a configuration the same or similar to that described herein may have a wicking member 15 and withdrawal cord 12 attached thereto via a line of lockstitching 40, and folded along longitudinal fold lines and subsequently molded under a combination of moisture control, applied heat and applied pressure and thereby compressed (as indicated by the arrows in FIG. 5E) to form it into a self-sustaining cylindrical or capsule-shaped form.

Figure 3B:
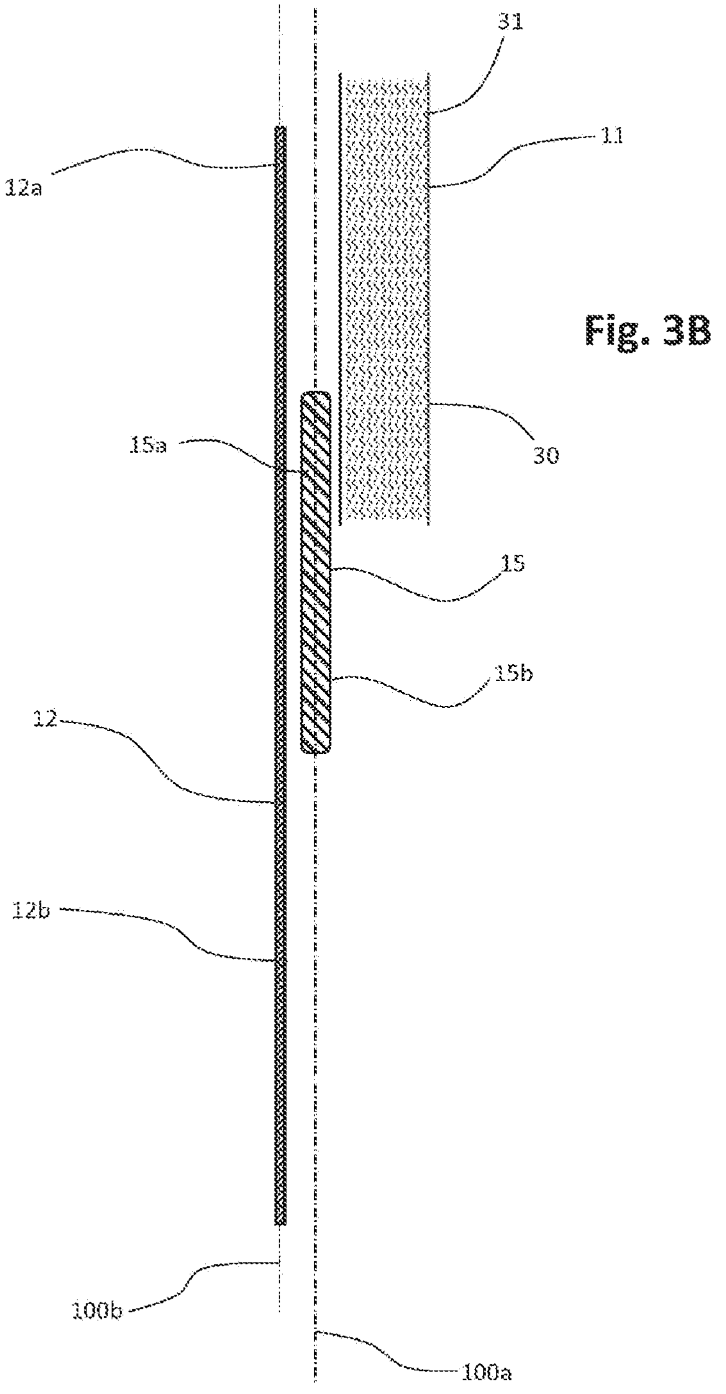
FIG. 3B is an exploded longitudinal cross section of components of the tampon shown in FIG. 2, taken through line 3B-3B in FIG. 2, and shown with the components separated, i.e., not joined together by stitching or other joining mechanism.

The pledget contemplated herein may have any suitable form and structure, for example, as depicted in FIGS. 2, 3A and 3B. Other non-limiting examples of suitable pledget form, material composition and structure are depicted and described in US2010/0268182 and US2007/0260211.

A wicking member 15, described in greater detail below, may be joined to either a withdrawal cord 12, the pledget 11 itself, or both. This joining of the wicking member may occur subsequently to compression of the pledget 11 to a self-sustaining form. In some variations it may be desirable to attach some or all of the wicking member 15 to the pledget 11, the withdrawal cord 12, or both, prior to compression of the pledget 11 to a self-sustaining form. In one method of making of a tampon 10, described more fully below, the wicking member 15 may be integral with the pledget 11 prior to compression of the pledget. In any of the above mentioned manners of construction, the trailing portion 15*b* of wicking member 15 is preferably not compressed with the pledget 11; or, if compressed, is not compressed to the same degree as the pledget 11.

Prior to formation into a self-sustaining form, the pledget 11 may be of any suitable shape, size, material, or configuration. In the non-limiting example shown in FIGS. 2, 3A and 3B, pledget 11 includes a batt or other mass of absorbent material 31, disposed within an outer wrapper 30. This type pledget may be formed on a continuous processing line wherein absorbent fibrous material is continuously deposited (e.g., via an airlaying process) to form a continuous batt having a desired cross-direction width and depth/weight, on a continuous web of wrapper material being conveyed along a machine direction. The wrapper material web may then be wrapped about the batt by suitable web guiding equipment, and affixed to itself via, e.g., adhesive, to form a continuous wrapped batt. Individual pledgets may then be cut from the continuous batt by repetitive die cutting across the moving batt (i.e., cutting along the cross direction). The cross-direction cuts may be linear, which will result in rectangular pledgets. Alternatively, as suggested in FIG. 2, the cross-direction cuts may be non-linear; in the example depicted, the cutting tool may be configured to make cuts forming the respective forward and rearward ends of each successive pledget, having an arched or curved profile. For a pledget of the configuration depicted, this curved profile, or in a slight modification, a cut profile that will impart the uncompressed pledget with a chevron shape, helps facilitate subsequent compression and formation into a cylindrical or capsule-shaped form with rounded or otherwise tapered forward and rearward ends, through the graduating reduction or tapering down, via the cut profile, in the bulk/quantity of material that must be compressed at each end. Other shapes that embody a tapering down of the quantity of material present toward the forward and rearward ends of the pledget are also contemplated.

While the pledget 11 shown in FIG. 2 is approximately chevron-shaped, other shapes such as but not limited to rectangular, trapezoidal, triangular and hemispherical may be used for tampons within contemplation of the present disclosure. It may be desired, however, that the cut profile be configured to form respective rear and front cut ends of respectively leading and trailing pledgets being cut from the batt as it moves through the manufacturing line, with no generation of cutoff waste/scrap. It can be appreciated that the non-limiting example of an end cut profile reflected in FIG. 2 provides this benefit.

In other examples (not specifically shown), the pledget 11 may be a laminar structure including integral or discrete layers. As noted, in the example shown in FIGS. 2, 3A and 3B, the pledget 11 may include an enveloping wrapper 30 and one or more layers of absorbent material 31 positioned within the wrapper. In other examples, the pledget need not have a layered structure at all. To facilitate compression into its self-sustaining form the pledget 11 may be folded, e.g., as depicted herein, may be rolled (e.g. as in currently marketed U BY KOTEX® brand tampons, a product of Kimberly-Clark Worldwide, Inc., Irving, TX), may comprise a "petal" structure (e.g. of overlaying/underlaying, crossing rectangular patches of absorbent material, in a configuration present in PLAYTEX SPORT® brand tampons, a product of Edgewell Personal Care LLC, Chesterfield, MO) or any other of the structures and configurations which are known in the art relating to tampon pledgets and their manufacture.

The pledget 11 and absorbent material 31 therein may include a wide variety of liquid-absorbing materials commonly used for absorbency in absorbent articles, such as rayon fiber, cotton fiber, or comminuted wood pulp fiber (sometimes called "airfelt"). Examples of other suitable absorbent materials may include creped cellulose wadding; spun and/or meltblown polymer fibers or filaments; chemically stiffened, modified or cross-linked cellulosic fibers; other synthetic fibers such as polyamide fibers (e.g., nylon fibers); peat moss; absorbent foams (such as open-celled foam formed through polymerization of a high internal phase water-in-oil emulsion); nonwoven web materials of natural and/or synthetic fibers or combinations thereof, tissue including tissue wraps and tissue laminates; or any equivalent material or combinations of materials, or blends or combinations of these. Suitable rayon fibers may include but are not limited to viscose, MODAL, TENCEL® (or lyocell); tri-lobal and conventional rayon fibers, and needle punched rayon). Suitable cotton fibers may include long fiber cotton, short fiber cotton, cotton linters, T-fiber cotton, card strips, and comber cotton. Preferably, the cotton fibers or fabric layer thereof should be scoured (for removal of natural hydrophobic waxes and impurities) and bleached (for whiteness) and may be imparted with a glycerin finish (for enhancing compaction), a leomin finish (for lubricity), or other suitable finish. Additionally, superabsorbent materials, such as superabsorbent polymers or absorbent gelling materials may be incorporated into the pledget. In particular examples it may be desired that rayon or cotton or a blend thereof, form the greater proportion (by weight) of the absorbent material 31, or that rayon alone form the greater proportion (by weight) of the absorbent material 31, since rayon fibers may possess absorbency properties or capacity greater than those of other fibrous materials, per unit weight and/or per unit cost.

In the example shown in FIGS. 2, 3A and 3B, the pledget 11 may be formed of a body of soft absorbent fibrous material such as rayon fibers or cotton fibers or a combination or blend thereof, and the wrapper 30 may be formed of a woven, knitted or nonwoven web fabric material of suitable composition. The materials for the body may have the form of nonwoven or woven fabric or a batt formed by any suitable process such as airlaying, carding, wetlaying, hydroentangling, or other known fiber deposition and consolidation techniques.

The absorbent material of the pledget 11 may be surrounded with a liquid permeable wrapper 30. Wrapper materials may include rayon, cotton, spunbond monocomponent, bicomponent or multicomponent fibers, or other suitable natural or synthetic fibers known in the art. If the pledget 11 is layered, the layers may include different materials. For example, in the example shown in FIG. 2 the wrapper 30, may be constituted primarily of rayon, while the absorbent material 31 may be constituted primarily of cotton. In other examples the wrapper may be constituted primarily of cotton, and the intermediate layer or layers may be constituted primarily of rayon. Optionally, the entire pledget 11 may be formed of a uniform or nonuniform blend of materials throughout. In another particular example, wrapper 30 may be formed of a nonwoven web of spunbond fibers. The spunbond fibers may be spun from, for example, polymer resin including polyolefins such as polypropylene, polyethylene, or a blend or combination thereof. In a more particular embodiment the spunbond fibers may be spun bicomponent fibers including a first polypropylene resin component and a second differing polypropylene resin component or a polyethylene resin component. When formed of ordinarily hydrophobic materials such as polyolefins (including polypropylene and polyethylene) wrapper 30 material may be treated, e.g., by application of a suitable surfactant, to render it hydrophilic, so that it will readily attract and permit aqueous fluid to wick therethrough to the absorbent material within the wrapper. A nonwoven web material formed of polymeric material as described may be desired to form the wrapper, over natural fibrous materials or semi-synthetic rayon, for reasons of having a soft, smooth and comfortable feel and low friction against sensitive skin and internal tissues, relatively low cost and superior wet structural integrity.

The pledget 11 may have any suitable size, shape and thickness that will both provide a suitable quantity of absorbent material and resulting absorption capacity, while permitting compression into a self-sustaining form of a size and shape suitable for easy and comfortable insertion. An uncompressed, opened size similar to those of conventional currently available tampons has been found to work well. A typical size for an uncompressed pledget may be from about 2 cm to about 8 cm in longitudinal length and from about 3 cm to about 8 cm in lateral width, including any combination of length and width within those ranges, in combination with an uncompressed thickness anywhere from about 1 cm to about 3 cm. Total basis weight for a flat, uncompressed and open pledget, may be from about 150 g/m2 to about 1,400 g/m2, calculated as the weight of the pledget divided by the largest surface area on one side of the pledget. Optionally, a pledget 11 that is shorter and wider than the ranges given above may also be desired in some circumstances to promote relatively greater swelling/expansion in a lateral or radial direction during use.

A withdrawal cord 12, configurations of which are depicted in the figures, is preferably joined to the pledget to facilitate withdrawal of the tampon from the vagina following a desired duration of use. The withdrawal cord 12 may having a leading portion 12*a* joined to the pledget 11 and a trailing portion 12*b* extending beyond the rearward end 17 thereof. In other examples, the withdrawal cord may be integral with the pledget, or an extension of a structural component of the pledget, such as of an overwrap as described above. In some examples the withdrawal cord 12 may be integral with a wicking member 15.

In a particular example, the withdrawal cord 12 may be a separate section of cord, string, yarn, ribbon, knitted cord or strip of woven or nonwoven fabric formed separately of the components of the pledget and wicking member, and then attached by any suitable mechanism to the pledget and/or to the wicking member.

The attachment mechanism may include sewing, adhesive attachment, thermal or pressure bonding, through-pledget punching, penetration and/or looping of the withdrawal cord material about structure(s) of the pledget or portions thereof, or any combination of these. A leading portion 12*a* of the withdrawal cord 12 may be attached or joined to any suitable location on the pledget 11, although it may be preferable that the attachment/joining location be substantially laterally centered on the pledget and proximate to, or include a location proximate to, the rearward end 17 of the pledget, so that tensile withdrawal force in the cord, exerted by the user, acts predominately on the rearward end of the pledget and does not tend to substantially rotate or reorient the pledget within the user's body during withdrawal. In the example shown in FIGS. 2, 3A and 3B, a leading portion 12*a* of the withdrawal cord 12 is joined to the pledget 11 along the length of the pledget 11, and trailing portion 12*b* trails free beyond the rearward end 17 of the pledget 11. The withdrawal cord 12 may be attached to the tampon pledget 11 while the pledget 11 is still uncompressed, as shown in FIG. 2. The withdrawal cord 12 may be attached along substantially the entire length of one major surface of the pledget 11.

Figure 4A:
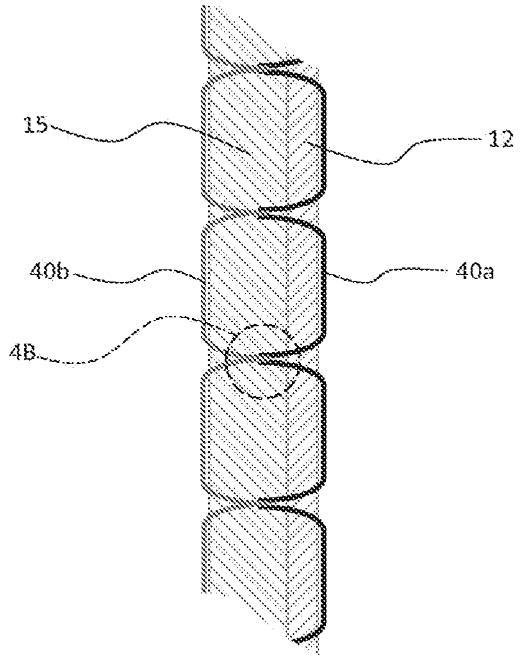
FIG. 4A is a longitudinal cross section of portions of a wicking member and withdrawal cord of the tampon shown in FIG. 2, taken through line 4-4 in FIG. 2.
Figure 4B:
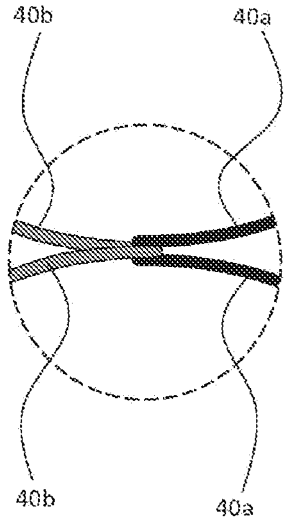
FIG. 4B is an enlarged view of portion of lockstitching shown within circle 4B in FIG. 4A.
Figure 5A:
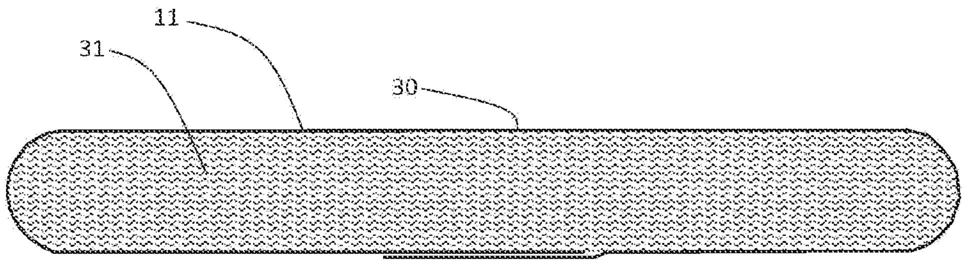
FIG. 5A is a lateral cross section of an example of a pledget prior to attachment of a withdrawal cord or wicking member.
Figure 5B:
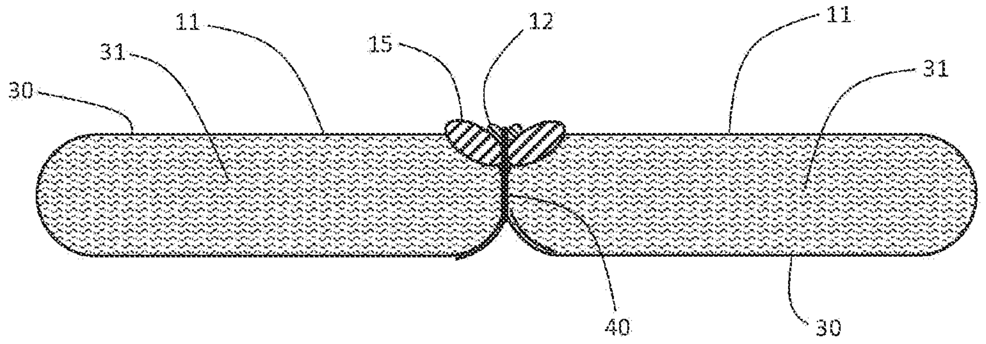
FIG. 5B is a lateral cross section of an example of a tampon including the pledget shown in FIG. 5A, following attachment of a wicking member and withdrawal cord via stitching.
Figure 5C:
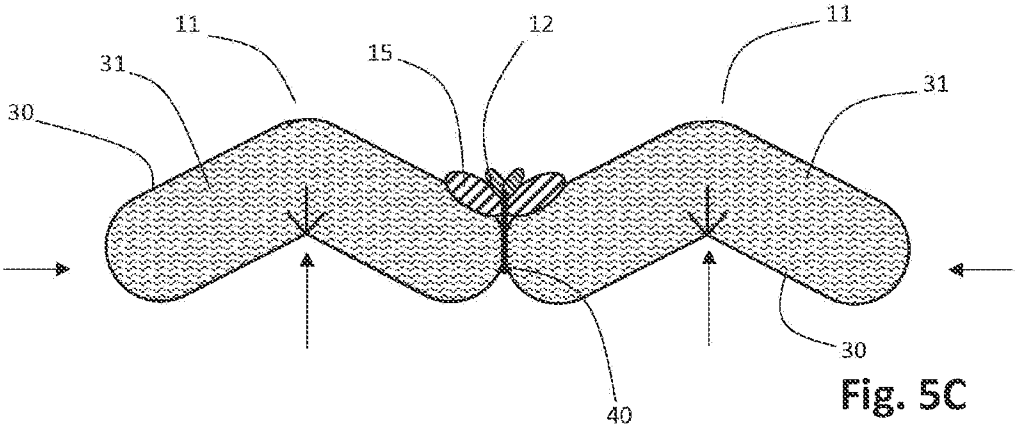
FIG. 5C is a lateral cross section of the tampon shown in FIG. 5B, shown at a time proximate commencement of folding as a step to formation of the pledget into a self-sustaining form.
Figure 5D:
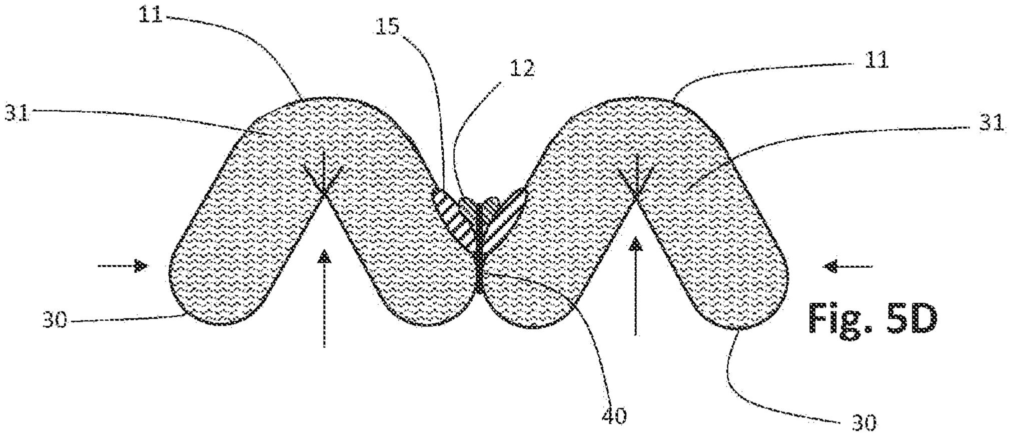
FIG. 5D is a lateral cross section of the tampon shown in FIG. 5B, shown at a time during folding as a step to formation of the pledget into a self-sustaining form.
Figure 5E:
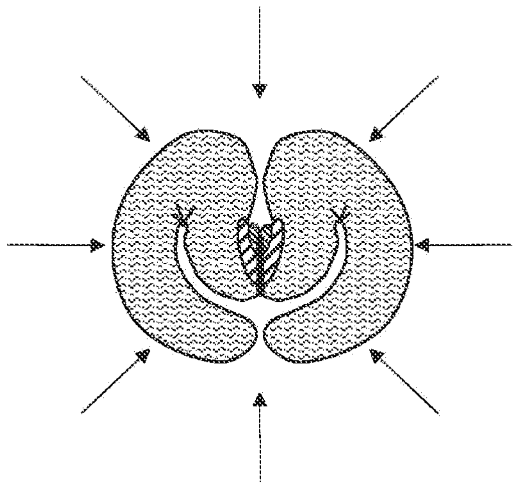
FIG. 5E is a lateral cross section of the tampon shown in FIG. 5B, shown at a time following folding and during radial compression as a step to formation of the pledget into a self-sustaining form.
Figure 7:
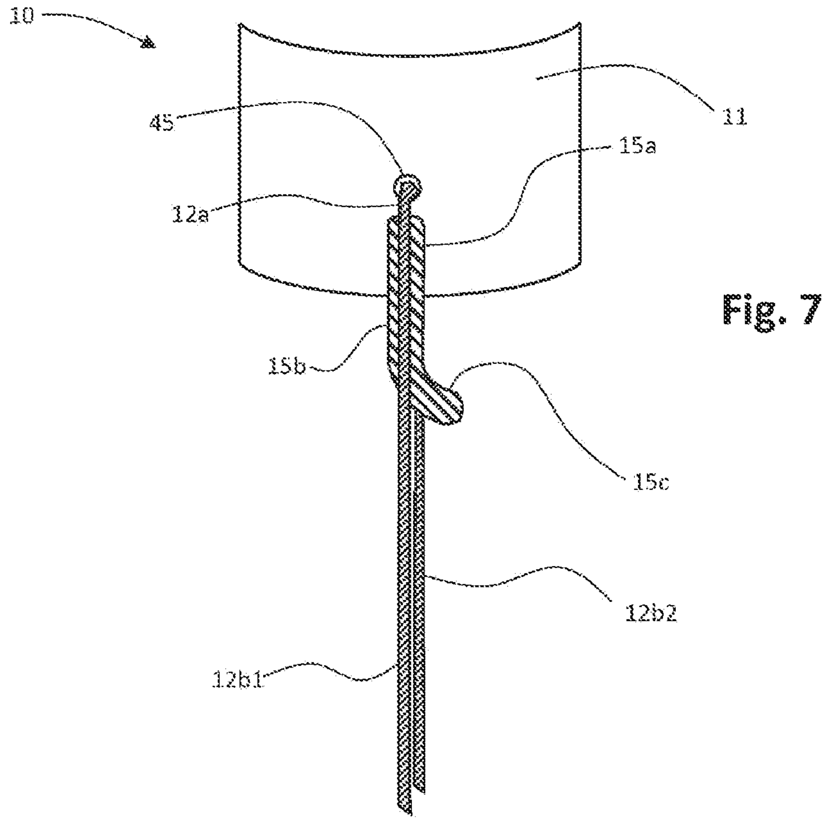
FIG. 7 is a longitudinal front side view of an example of a tampon before the pledget has been shaped and compressed into a self-sustaining form, depicting an alternative configuration for connection of a withdrawal cord to the pledget.
Figure 8:
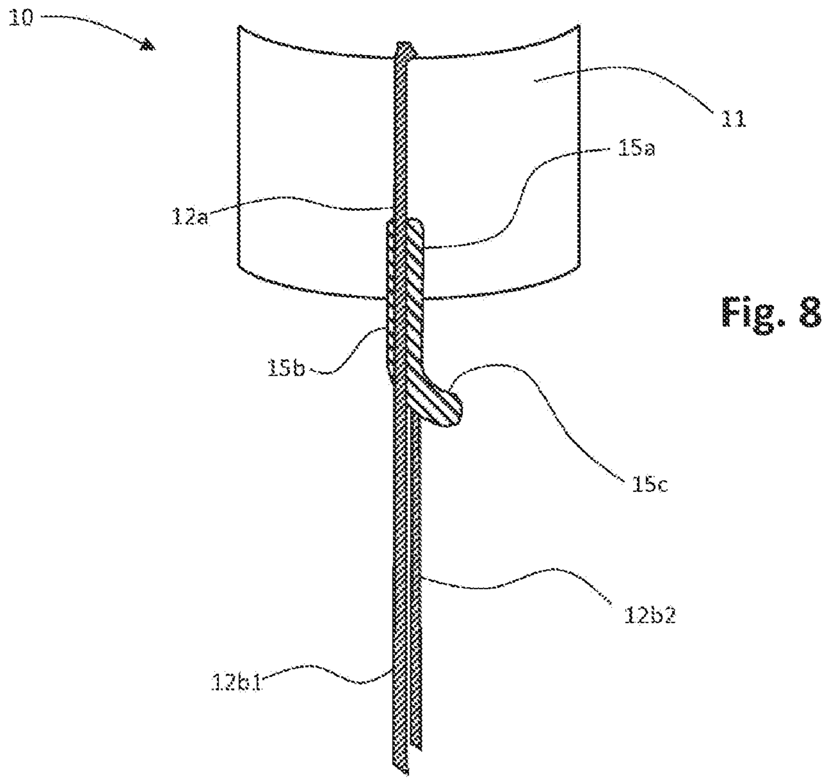
FIG. 8 is a longitudinal front side view of an example of a tampon before the pledget has been shaped and compressed into a self-sustaining form, depicting another alternative configuration for connection of a withdrawal cord to the pledget.

To minimize chances of failure of the attachment between the withdrawal cord 12 and the pledget (i.e., separation) during withdrawal, it may be desired that the withdrawal cord be directly or indirectly attached along substantially the entire length of the pledget, thereby diffusing tensile withdrawal force exerted by the user, by distributing it over the length of the pledget. To further minimize chances of failure of the attachment, it may be desired that the attachment mechanism include a longitudinal line of lockstitching 40 in which stitches entirely penetrate the withdrawal cord 12 and the pledget (through both sides), thereby connecting and affixing the withdrawal cord through a substantial portion of the structure of the pledget, rather than only to an outer surface thereof. Such attachment further diffuses withdrawal force through the body/structure of the pledget. In other examples, a length of withdrawal cord stock may be threaded through a portion of the body/structure of the pledget (e.g., through a hole 45 punched therethrough), looped around and doubled to create pair of trailing portions 12*b*1, 12*b*1. (See, e.g., FIG. 7.) In still other examples, a length of withdrawal cord stock may be looped around a substantial portion of the pledget body without punching, and doubled to create pair of trailing portions 12*b*1, 12*b*1. (See, e.g., FIG. 8.) Trailing portions 12*b*1 and 12*b*2 may be tied and knotted or otherwise affixed together. These latter two approaches also may be employed to provide a secure connection between the pledget and the withdrawal cord.

Where lockstitching is used to attach the withdrawal cord to the pledget, it may be desired that the line of lockstitching 40 extend longitudinally along substantially the entire length of the withdrawal cord 12 (including both leading and trailing portions 12*a*, 12*b*). In examples in which the withdrawal cord 12 is formed of a section of twisted, braided or knitted strands or fibers, lockstitching that traverses substantially the entire length of the withdrawal cord may be desired because the thread strands forming the stitches through the cord are effectively intertwined with component fibers and/or strands of the cord, and can thereby function to substantially prevent the cord from unraveling from its cut ends. Herein, a line of "lockstitching" means a line of stitches formed of at least two strands of thread 40*a*, 40*b* disposed on opposing sides of the body(ies) to be stitched together, wherein stitches are sequentially formed as each thread meets and loops around the other, via passage through the body(ies) by one or both threads, at suitable intervals corresponding to the desired size of the stitch. In some examples, a first thread may be sequentially passed through the body(ies) to meet the second thread via use of an appropriate sewing needle, while the second thread is looped about the first thread by operation of a looper. Chainstitching consisting of two threads as described above is included within the definition. A non-limiting example of lockstitching may be seen in FIGS. 4A and 4B, depicting a longitudinal cross section through a wicking member 15 and withdrawal cord 12, wherein these two components are held together by a longitudinal line of lockstitching with stitches formed by front thread 40*a* and rear thread 40*b*. FIGS. 4A and 4B depict ISO #301 type lockstitching, as specified by the International Organization for Standardization, ISO 4519:1991, as an example. Other types of lockstitching may be preferred in some circumstances, for example, ISO #401 type chainstitching, which may further enhance the stitches' ability to resist unraveling themselves, and prevent unraveling of the stitched withdrawal cord and/or wicking member, at cut forward and/or rearward ends thereof.

In some circumstances in which the line of lockstitching exists along a length of the trailing portion 12*b* of the withdrawal cord, it may be desired that the threads used to form the line of lockstitching be made of a suitably hydrophobic fiber material, or fiber material treated to be suitably hydrophobic, so that the lockstitching thread is unlikely to wick fluid along the trailing portion of the withdrawal cord.

In some examples the lockstitching thread may be formed of or include cotton fiber, processed or treated to be suitably hydrophobic. In some examples the lockstitching thread may be formed of or include polyester fiber (which in some formulations may be inherently somewhat hydrophobic). In some examples the lockstitching thread may be formed of or include a blend of cotton fiber and polyester fiber, wherein the cotton fiber may be processed or treated to be suitably hydrophobic.

The tampon 10 may also be provided with multiple withdrawal cords 12. For example, two withdrawal cords 12 may be attached down the length of the pledget 11 and extend from the withdrawal end thereof. In such an instance, the wicking member, may be joined to one or both of the withdrawal cords 12.

Especially when the wicking member 15 is joined to the withdrawal cord 12, the withdrawal cord 12 is preferably non-absorbent along at least the location of such attachment. As used herein, the term "non-absorbent" refers to a structure formed predominately of suitably hydrophobic materials such it does not tend to attract, wick or retain any substantial quantity of fluid within its structure. In some examples it may be desired that substantially the entire withdrawal cord 12 be hydrophobic, so that the withdrawal cord does not wick menstrual fluid along its trailing portion 12*b*, potentially out to its trailing end. The materials comprising the withdrawal cord may be inherently non-wettable or hydrophobic, or they may be treated to provide such properties. For example, a suitable wax may be applied to the withdrawal cord 12 to decrease or eliminate wicking tendency. Other means for providing a material suitable for use as a withdrawal cord 12 which is non-absorbent and/or non-wicking are known in the art. For example, U.S. Pat. No. 5,458,589 describes one such approach. However, the withdrawal cord 12 need not necessarily be non-wicking along its entire length, even if a non-absorbent withdrawal cord is desired. For example, it may be desirable to provide a withdrawal cord 12 in which at least a portion of the cord has a tendency or capability to wick deposited fluid upwardly toward the rearward end 17 of the pledget and into the structure thereof.

The withdrawal cord 12 need not have uniform properties throughout its length. For example, the portion of the withdrawal cord nearest the pledget 11 may be manufactured and/or treated so as to have wicking capability, while the lower portion (i.e. furthest from the pledget 11) of the withdrawal cord 12 may be manufactured and/or treated so as to not have wicking capability. Other properties such as hydrophilicity/hydrophobicity, density, capillary size, width, thickness, and the like may also vary along the length of the withdrawal cord 12.

The withdrawal cord 12 may be formed of a strand or strands of component yarn or thread material. In some examples the yarn or thread material may be formed of cotton fiber, cotton fiber processed or treated to be suitably hydrophobic, other natural plant-based fiber which may be processed or treated to be suitably hydrophobic, or polyester, or a combination or blend thereof.

The component yarn or thread may be knitted, twisted or braided to form the withdrawal cord stock. For maximized tensile strength per unit decitex of the withdrawal cord stock, it may be desired that the component yarn or thread be of twisted or braided construction (rather than of knitted, woven or other construction).

The tampon 10 also may be provided with a wicking member 15. A leading portion 15*a* of the wicking member may be attached along a portion or length of the pledget 11 and may have a trailing portion 15*b* extending or trailing by a suitable length from the rearward end 17 of the pledget. The wicking member 15 may be separate from, or joined to, the withdrawal cord 12 along a portion or all of their respective lengths. As will be discussed below, the wicking member 15 may be provided, following insertion of the tampon at a suitable location within the vaginal cavity, to extend rearward of the rearward end of the pledget, further down the vaginal cavity toward the introitus, where it can be in position to contact menstrual fluid that may be present below the pledget, and attract and wick liquidous components thereof up to the pledget 11.

The wicking member 15 may be formed of a suitable configuration of fibrous material having suitable fluid handling properties and tensile strength. It may be desired that the wicking member be formed separately of the withdrawal cord, and of one or more material(s) distinct from the one or more materials forming the withdrawal cord. As discussed above, in some examples it may be desired that the material(s) forming the withdrawal cord be suitably hydrophobic, to reduce or avoid wicking of fluid along the withdrawal cord. This is contraindicated by the requirements for the wicking member as discussed herein, and it may be desired that hydrophobic fibrous components of the withdrawal cord not be present within the structure of the wicking member, where they can contribute to obstructing or interrupting wicking. Accordingly, it may be desired that the respective structures of the wicking member and withdrawal cord not be coaxial and/or not intermingled. Rather, as suggested in the figures, the wicking member and the withdrawal cord may be arranged in contact with each other (or not) along a substantially parallel, non-coaxial configuration; see, e.g., FIG. 3B, depicting such a non-coaxial configuration, where the parallel longitudinal axes 100*a*, 100*b* of the wicking member 15 and withdrawal cord 12, respectively, are not the same.

Tampons of the type and configurations contemplated herein may also have or include any combination of features described in U.S. Application Ser. No. 62/780,388, filed on Dec. 17, 2018 by Strong et al. and/or U.S. Application Ser. No. 62/834,427, filed on Apr. 16, 2019 by Strong et al.

The ability and tendency of a fibrous structure to draw in and transport (herein, "wick") aqueous fluid against external forces acting on the fluid (such as gravity) is a function of several features of the structure. These include the extent of hydrophilicity of the surfaces of the fibers; the extent of capillarity within the structure (where capillarity relates to the number and average size and volume of interstitial spaces constituting potential fluid passageways between and among the fibers, resulting from the extent and manner of fiber consolidation in the structure); the complexity of the fibers' surface geometry(ies); and the extent to which the structure has already drawn in and retains (i.e., has absorbed) fluid. Capillarity of a fibrous structure relates to the amount of fiber surface area that is present within the structure, per unit volume of the overall structure, and to the density of consolidation of the fibers in the structure, which affects the size and volume of the interstitial spaces or fluid passageways. The size and volume of the interstitial passageways affects the degree to which the aggregate attractive pull of the hydrophilic fiber surfaces in contact with the fluid can overcome forces that resist it, i.e., surface tension of the fluid and external forces such as, e.g., gravity or pressure differential. For example, for a structure formed of a given fiber composition, interstitial passageways which are too large can make the structure ineffective at wicking upward against gravitational pull because there is an insufficient aggregate area of hydrophilic fiber surfaces in contact with the fluid to create attractive pull sufficient to overcome gravitational pull acting on the relatively large fluid volume and mass in the relatively large passageways, and surface tension of the fluid mass itself tending to resist separation into smaller fluid volumes. On the other hand, interstitial passageways which are too small and/or insufficient in aggregate volume such that, while effective at moving fluid in small volume, can be physically restrictive with respect to wicking volume flow rate. For a given type of hydrophilic fibers, there will be an optimum capillarity in a structure formed of them, at which wicking potential is maximized.

Further, the composition of human menstrual fluid differs from pure water or typical saline test solution in ways (e.g. surface tension) that cause the fluid to behave differently than water or saline solution with respect to wicking structures and absorbent structures. For this reason, a given structure may more readily and/or rapidly wick or absorb a greater quantity of water or saline than menstrual fluid, and vice versa. For purposes herein, wicking and absorption of human menstrual fluid, relevant compositional aspects of which are herein deemed suitably approximated by defibrinated sheep's blood under conditions described herein, are of interest and focus. For a structure formed of a given fiber composition there will be a level of fiber consolidation that optimizes capillarity and wicking performance under these conditions.

Wicking and absorption are relatively complex phenomena and can be difficult to precisely measure and characterize for many types of structures. However, it may be observed, generally, that: (1) between two dry fibrous structures formed of identically composed fibers having similar hydrophilicity, the structure with the more optimal capillarity will have the greater wicking performance; (2) between two dry fibrous structures formed of fibers of differing compositions but having similar capillarity, the structure formed of the fibers having greater hydrophilicity will have the greater wicking performance; (3) between two wetted fibrous structures having similar capillarity, formed of fibers of the same composition and having similar hydrophilicity, the structure holding the lesser quantity of aqueous fluid per unit structure volume will have the greater wicking potential. Between two differing first and second fibrous structures that are placed in contact with each other, the first structure will draw fluid from the second structure if the first structure has a combination of hydrophilicity, capillarity and level of fluid content (saturation) per unit structure volume that impart to it greater wicking potential than the second structure. Conversely, if the first structure has lesser wicking potential than the second structure, the first structure will not draw fluid from the second structure.

Thus, it may be desired that the component fibrous material of the wicking member 15 have a combination of fibers with hydrophilic surface properties, and optimized capillarity, to promote wicking of fluid therealong, but at the same time, not have, or not be assembled in a configuration having, a combination of capillarity and hydrophilicity that render it more likely to attract and retain menstrual fluid against the wicking potential of the material(s) of the pledget 11. It is preferred that the material of the wicking member serve to wick fluid to the pledget, but that the material(s) of the pledget have greater wicking potential and absorbency so as to be effective at drawing menstrual fluid from the wicking member over the expected normal duration of use of the tampon.

In some examples the wicking member may be formed of fibrous material(s) similar to those used to form the pledget, e.g., rayon fibers, absorbent cotton fibers or any combination thereof. In such examples the fibrous material forming the wicking member pledget should be configured such that the body of the wicking member has less wicking potential than the pledget. The wicking potential of the wicking member can be adjusted by the selection of material of which it is formed, for its relative level of fiber surface hydrophilicity and its relative capillarity. Capillarity may be adjusted by the manner in which the fibers forming the wicking member are consolidated and densified within in the structure.

It has been discovered that a non-hydrophilic (i.e., hydrophobic) fibrous material can be effectively treated and configured to serve the desired wicking function while in most circumstances having less affinity for the fluid than typical pledget materials (i.e., rayon fiber and/or cotton fiber). Spun polymeric synthetic fibers that are ordinarily hydrophobic, such as spun polypropylene fibers, may be treated, e.g., via application of a suitable surfactant finish, to render their surfaces hydrophilic. Since such fibers typically have simple and/or smooth surface geometry, however, the fiber surfaces themselves do not substantially contribute to capillarity, and bundles or assemblies of such fibers will have substantially less wicking potential (and tendency to retain the fluid) than bundles or assemblies of more complexly-shaped hydrophilic fibers such as rayon, cotton, or other natural plant-based fibers. Accordingly, in some examples it may be desired that the wicking member be formed of fibrous material including spun polypropylene or other spun polymeric synthetic polymer. Additionally, braided or twisted bundles of polypropylene fibers may be rapidly cut in a cross-direction to form individual wicking members to be placed and affixed to tampons, in a manner in which fibers are crushed together and pinched off, rather than cleanly severed at each cut. Under such circumstances, the polypropylene fibers can be caused to plastically deform and flow about each other at the pinch/cut location. For wicking material stock of braided or twisted configuration, this may help reduce unraveling of the wicking member at the cut end(s).

For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

While a tampon with a wicking member may absorb some menstrual fluid into the wicking member and may even wick fluid to the pledget to some extent, it is believed from research that the effectiveness of the combination may not be meaningfully noticeable to a user unless its ability to capture and wick fluid through the wicking member up to the pledget exceeds a particular value for Wicking as set forth and described herein. A combination of materials described herein, used to constitute and configure a tampon product, may be selected and assembled as described to provide a tampon that will wick at least 1.2 grams, more preferably at least 1.5 grams and even more preferably at least 1.8 grams of test fluid up through the wicking member as measured using the Wicking Measurement method herein. Information herein and also as known in the art is sufficient to enable one to select materials for the pledget and for the wicking member to achieve these levels of wicking. If the material of the wicking member has an insufficient combination of suitable hydrophilicity and capillarity, it will be unable to attract and wick menstrual fluid upwardly to the pledget to the levels specified herein, under the conditions of the measurement method (which are designed to approximate the orientation of the tampon and pressure to which its materials are subjected when the tampon is in use, disposed in the vaginal cavity). For this reason, a wicking member formed of polymeric fibers, for example, that have not been suitably processed or treated to render them suitably hydrophilic, have insufficient longitudinal directional orientation, and/or are too loosely or too densely consolidated, will be ineffective. On the other hand, if the material of the wicking member has a combination of hydrophilicity at a suitable level and capillarity that makes it have a greater affinity for fluid contained therein than can be overcome by the wicking potential of the pledget, the pledget will be unable to draw fluid away and out of the wicking member, and once saturated, the wicking member will cease wicking. For this reason, a wicking member formed primarily of, for example, completely scoured cotton and/or rayon fibers (which have a high affinity for aqueous fluid and therefore form structures that are relatively highly absorbent) may be unsatisfactory. The ability of the pledget to draw fluid from the wicking member may be further enhanced by processes and configurations described in U.S. provisional patent application Ser. No. 62/683,661. A balance between wicking potential of the pledget and wicking potential of the wicking member may be identified to meet the wicking levels specified above. It has been learned that a level of measured wicking at one or more levels specified above is greater than that achieved by currently available tampons that include wicking structures. It is believed that a level of measured wicking at levels specified above represents improvement in the performance of tampons with wicking structures, in preventing bypass leakage or leakage of residual fluid in the vaginal cavity present following removal of a used tampon. Using combinations of materials described herein, the inventors have achieved measured wicking as high as 2.3 grams, although it is contemplated that greater levels as high as 3 grams, 4 grams or even 5 grams may be achievable through experimentation, using suitable combinations of materials and configurations identified herein or otherwise known to the person of ordinary skill in the art.

In order that the wicking member provide continuous, substantially uninterrupted and generally longitudinally-directed pathways for relatively rapid fluid travel along the length of the wicking member, it may be desired that the configuration of fibrous material be formed of carded or otherwise directionally aligned fibers, predominately aligned along the length of the wicking member 15 (along the longitudinal direction). In some examples, the wicking member may be formed partially, predominately or entirely of tow fibers that predominately extend substantially the entirety of the length of the wicking member 15.

In some examples, the wicking member may have the form of a strip of nonwoven, woven or knitted cloth, or ribbon. However, for purposes of maximizing the presence of generally longitudinally-oriented fluid pathways for wicking fluid to the pledget, it may be desired that the fibers forming the wicking member are predominately longitudinally oriented or biased, and held together by twisting (in the manner in which twisted yarn or rope is formed), or by braiding, rather than by other techniques such as needlepunching, hydroentangling, rolling, knitting, weaving, etc. A braided or twisted configuration, in combination with substantially directionally-aligned carded and/or tow fibers, may help increase the presence, number and length of generally longitudinal pathways through and along the fibrous material forming the wicking member, along which fluid may travel more directly along hydrophilic surfaces thereof toward the pledget.

When the wicking member is formed of fibrous material, and has cut forward and/or rearward ends, it may be desired that the fibrous material at one or both of forward and rearward ends be consolidated and bound together ("finished") via a mechanism that effectively reduces chances of the occurrence, or reduces the extent to which, the fibrous material may unravel or dislodge at the cut ends. In non-limiting examples, in which the wicking member includes or is formed of fibrous material manufactured from thermoplastic resin, fibers proximate one or both the forward and rearward ends of the wicking member may be fused, welded or otherwise bonded together by, e.g., application of heating energy and/or pressure during or following cutting. It will be appreciated that other mechanisms may serve, such as, but not limited to, knotting the cut end, applying a binder or adhesive to the cut end, etc.

The wicking member 15 may have any suitable length, but its trailing portion **15*b* (the portion extending rearward of rearward end 17 of pledget 11) is preferably shorter than the trailing portion of the withdrawal cord 12. The trailing portion of the wicking member should not be long enough extend through the introitus when the tampon 10 is fully inserted and properly positioned within the vaginal cavity. Although dimensions of the vaginal cavity vary among individual users, it may be desired for most users that the trailing portion 15*b* of the wicking member 15** should have a length no greater than about 60 mm, more preferably no greater than about 50 mm, even more preferably no greater than about 40 mm, and still more preferably no greater than about 30 mm, and preferably no less than about 10 mm, more preferably no less than about 15 mm, and even more preferably no less than about 20 mm. (For purposes herein, the length of the trailing portion is measured with the trailing portion held in a straightened position, but in a relaxed condition, i.e., not under longitudinal tension greater than about 5 gf).

In order to ensure that an adequate portion of the surface area of the wicking member 15 is exposed to contact with the pledget (for purposes of facilitating movement of fluid from the wicking member to the pledget), it may be desired that the leading portion **15*a* have a length that is at least one-quarter of the total length of the pledget, and more preferably at least one-third of the total length of the pledget. In a particular example, the leading and trailing portions of the wicking member 15*a*, 15*b*** may be approximately equal in length. It may also be preferred that the leading portion of the wicking member be affixed to the pledget along a length that is at least 10 mm, and more preferably at least 15 mm.

To enhance unitized structural integrity of the tampon, it may be desired that the wicking member 15 be lockstitched to the pledget, in a manner such as described above. In some examples the withdrawal cord 12 and the wicking member 15 may be lockstitched together to the pledget, via the same configuration/line of lockstitching. In such configuration, it may be desired that the wicking member be disposed in direct contact with the pledget, and preferably that the wicking member be disposed between the pledget and with the withdrawal cord, to provide for direct contact and fluid transfer between the wicking member and the pledget, unobstructed by the (e.g., hydrophobic) structure of the withdrawal cord. In some examples, however, the wicking member 15 may be attached to the pledget 11 by a mechanism differing from that attaching the withdrawal cord 12 to the pledget 11, and may also be physically separated from the withdrawal cord 12 at or along location(s) of attachment on the pledget. In some examples, the wicking member 15 may be attached to the pledget 11 by adhesive bonds, by thermal compression or ultrasonic bonds (in which respective material(s) of the wicking member and of the pledget are fused or welded together) or may be stitched to the pledget by stitches separate from stitches attaching the withdrawal cord to the pledget 11.

Figure 6:
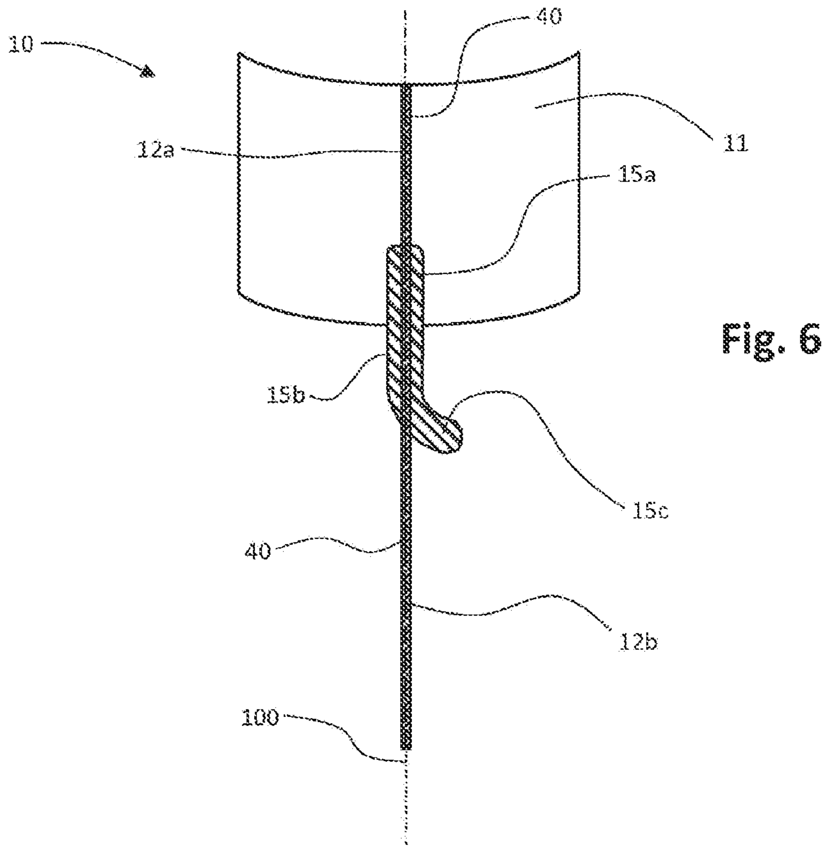
FIG. 6 is a longitudinal front side view of an example of a tampon before the pledget has been shaped and compressed into a self-sustaining form, with a wicking member having a free trailing end.

In some circumstances, it may be desired that a rearward, endward-most trailing portion of the wicking member 15 have a free length including a free end 15*c* that is not stitched or otherwise affixed to the withdrawal cord 12, as suggested in FIG. 6. This may further improve the ability of the wicking member 15 to capture and wick fluid to, into and/or through, its trailing portion 15*b*.

In some further examples, one or more threads used to stitch the wicking member 15 to the pledget 11 may be selected for suitable tensile strength and hydrophobicity such that they may be extended beyond the trailing rearward end of the wicking member by a suitable length, and by themselves serve as the withdrawal cord. This configuration eliminates the need for, and expense and complexity associated with including, a separate withdrawal cord. Where two or more stitching threads are used to lockstitch the wicking member to the pledget, they may be twisted, braided or otherwise suitably intertwined or combined into a singularized cord configuration in a trailing portion extending rearwardly from the wicking member.

It may be desired that the material used to form the wicking member be tinted or pigmented to impart the wicking member with a color that visibly contrasts with the color(s) of the materials forming the pledget and/or withdrawal cord. This may be deemed useful for visually signaling to the user that a differing material is present in the wicking member, suggesting a functionality distinct from that of the withdrawal cord. In connection with appropriate information on, or associated with, packaging for the tampon product, such tinting or pigmenting can advantageously serve to remind the user that the wicking member is present to provide supplemental protection against leakage. When the pledget and/or materials constituting the pledget have a substantially white color (which is, for example, the natural color for suitably processed, undyed cotton, and is believed to be preferred by many consumers because it connotes purity, cleanliness, sanitation and/or freshness), it may be desired that the material(s) constituting the wicking member are imparted with a non-white color that not only visibly contrasts with the color of the pledget, but also visibly contrasts with color(s) of areas of a pledget as stained by menstrual fluid as it may appear immediately following use. Thus, in some examples it may be preferred that the non-white color of the wicking member be selected from a range of colors that will visibly contrast with the color of the pledget, and with the color(s) of the pledget when stained by menstrual fluid, as it appears immediately following withdrawal of the tampon. This coloration feature may serve to provide the user with additional signal of the functionality of the wicking member. For purposes herein, "substantially white" means having CIE L*a*b* values when measured according to the Color Measurement Method set forth below, in which L* is ≥87, and the absolute values of each of a* and b* are ≤2. A wicking member color that visibly contrasts with the color of the pledget is any color that exhibits a $\Delta E^* \geq 15$ from the color of the pledget, measured according to the Color Measurement Method below. Techniques for imparting varying colors, and adjusting the depth thereof, to synthetic, semi-synthetic and natural plant-based fibers or filaments, or materials made therefrom (e.g., via use or inclusion of pigments, dyes or inks), are known in the art.

In an array of two or more packaged tampon products (herein "array" means two or more differing products of the same brand, marketed or appearing for sale simultaneously in the same or proximate respective locations (physical or online/virtual) (e.g., on the same or respective proximately located shelves within the same retail store)), differing wicking members can be included with tampons of differing features, for the purposes of functioning differently with the differing tampon products, signaling the differences in features to consumers, or a combination of both. In one non-limiting example, packaged tampons having a first absorption capacity may include wicking members imparted with a first color, while packaged tampons having a second, differing absorption capacity may include wicking members imparted with a second color visually distinguishable from the first color. For purposes herein, a second wicking member color is "visually distinguishable" from a first wicking member color when the second wicking member color exhibits a $\Delta E^* \geq 5$ from the first wicking member color, measured according to the Color Measurement Method below. Wicking members for an array of differing tampon products may differ not only in color, but in other characteristics such as material composition and/or absorbency/wicking characteristics, physical structure (e.g., braided, twisted, knitted, etc.), length, width, diameter, density, decitex or other dimension, location of attachment on the pledget, etc. The differing tampon products with respectively differing wicking members may be accompanied by associated packaging material imprinted with graphic/pictorial information, verbal information, or a combination thereof, that signals the differences in the respective products and/or wicking members.

A tampon as contemplated herein is believed to offer several advantages over prior art tampons. As noted previously, the incorporation of the wicking member 15 extends fluid capturing capability to lower regions of the vaginal cavity. Additionally, because the tampon can be manufactured by processes in which the wicking member is less compressed than the pledget 11, the material forming the wicking member can be available to immediately draw in fluid, without the need for re-expansion from a compressed state.

Tampons of the type and configuration(s) contemplated herein may be manufactured via the process described in U.S. Application Ser. No. 62/780,388, filed on Dec. 17, 2018 by Strong et al. and/or U.S. Application Ser. No. 62/834,427, filed on Apr. 16, 2019 by Strong et al.

To form a tampon ready for use, the tampon pledget 11 may be compressed and heat conditioned (which may include use of steam or elevated humidity) in any suitable conventional manner to impart it with a self-sustained form suitable for casy and comfortable insertion, which may be a cylindrical form. Pressures, temperatures and humidity conditions suitable for this purpose are known in the art. Typically, the pledget 11 is compressed in both the radial and axial direction using any suitable means known in the art. While a variety of techniques are known and acceptable for these purposes, a modified tampon compressor machine available from Hauni Machines, Richmond, VA, is suitable.

The tampon 10 contemplated herein may be inserted digitally or via the use of an applicator. If the tampon 10 is to be configured for digital insertion, or for insertion from a generally cylindrical applicator, it may be desirable to form the pledget from a layer of absorbent material which has been rolled or otherwise formed into a cylindrical or capsule shape.

Any of the currently available tampon applicators may also be used for insertion of the tampon contemplated herein. Such applicators of typically a tube-and-plunger type arrangement and may be plastic, paper, or other suitable material. A compact type applicator can also be suitable. The applicator plunger may be depressed by the user to push the compressed pledget 11 out of the applicator while fitting around the wicking member 15.

Color Measurement

The total color difference (ΔE*) between a tampon pledget 11 and its wicking member 15 is calculated from the L*a*b* color values obtained for each respective portion of the tampon. Color analyses are made using a 0°/45° spectrophotometer with adjustable apertures capable of making standard CIE L*a*b* measurements in accordance with ASTM E1349. An example of a suitable spectrophotometer is the Labscan XE (available from Hunter Associates Laboratory, Inc., Reston, VA, or equivalent). All testing is performed in a room maintained at a temperature of 23° C.±2.0° C. and a relative humidity of 50%±2% and samples are conditioned under the same environmental conditions for at least 2 hours prior to testing.

If the tampon is provided in an application, the test sample is prepared by first removing the tampon 10 from the applicator in the manner the product is designed to effect ejection of the tampon 10 from the applicator. The pledget 11 is flattened out by gently opening it from its self-sustaining shape. Using a small pair of scissors to sever any stitching as necessary, or using freeze spray to deactivate any adhesive used to join them, gently separate and remove the wicking member 15 from the pledget 11, using care so as not to damage either component in the process. For each product tested, a total of 5 pledgets and 5 wicking members are prepared in this manner.

To measure color, calibrate and standardize the instrument per the vendor instructions using the standard white and black tiles provided by the vendor. Set the spectrophotometer to use the CIE L*a*b* color space with a D65 standard illumination, a 10° observer, a 0.125 inch area view, a 0.200 inch aperture, and the UV filter set to nominal. Place the pre-flattened pledget test sample over the aperture such that the entire aperture is covered by the pledget 11 on an area free of the withdrawal string 40. Place the standard white tile behind the pre-flattened pledget test sample, take a reading and record L*a*b* values as $L_2*a_2*b_2*$ to the nearest 0.01 units. Remove the pledget test sample from the aperture and replace it with the wicking member test sample. Ensure that the entire aperture is covered by the wicking member, minimizing the amount of withdrawal cord 12 present in the aperture's viewing area. Place the standard white tile behind the wicking member test sample, take a reading and record L*a*b* values as $L_1*a_1*b_1*$ to the nearest 0.01 units. Calculate the total color difference (ΔE*) between the pledget and the wicking member as follows:

$$\Delta E^*=[(L_2^*-L_1^*)^2+(a_2^*-a_1^*)^2+(b_2^*-b_1^*)^2]^{1/2},$$

and record as ΔE* to the nearest 0.01 units.

In like fashion, repeat for a total of five measurements obtained on five different tampon pledget and wicking member samples. Calculate the arithmetic mean for ΔE* obtained from all five measurements and report to the nearest 0.01 unit.

Wicking Measurement

The ability of a tampon configuration with a wicking member to capture fluid in the wicking member, and wick and fluid to the pledget, may be measured using this Wicking Measurement method. A known quantity of test fluid is delivered at a constant rate over a specified amount of time to a portion of the wicking member 15 inside a pressurized wicking chamber. The quantity of fluid absorbed by the tampon 10 is determined and reported as Total Uptake. All measurement is performed in a laboratory maintained at 23° C.±2 C.° and 50%±2% relative humidity. The measurement equipment as described herein is configured to approximate the pressure to which a tampon is subjected inside the body during actual use.

Figure 9A:
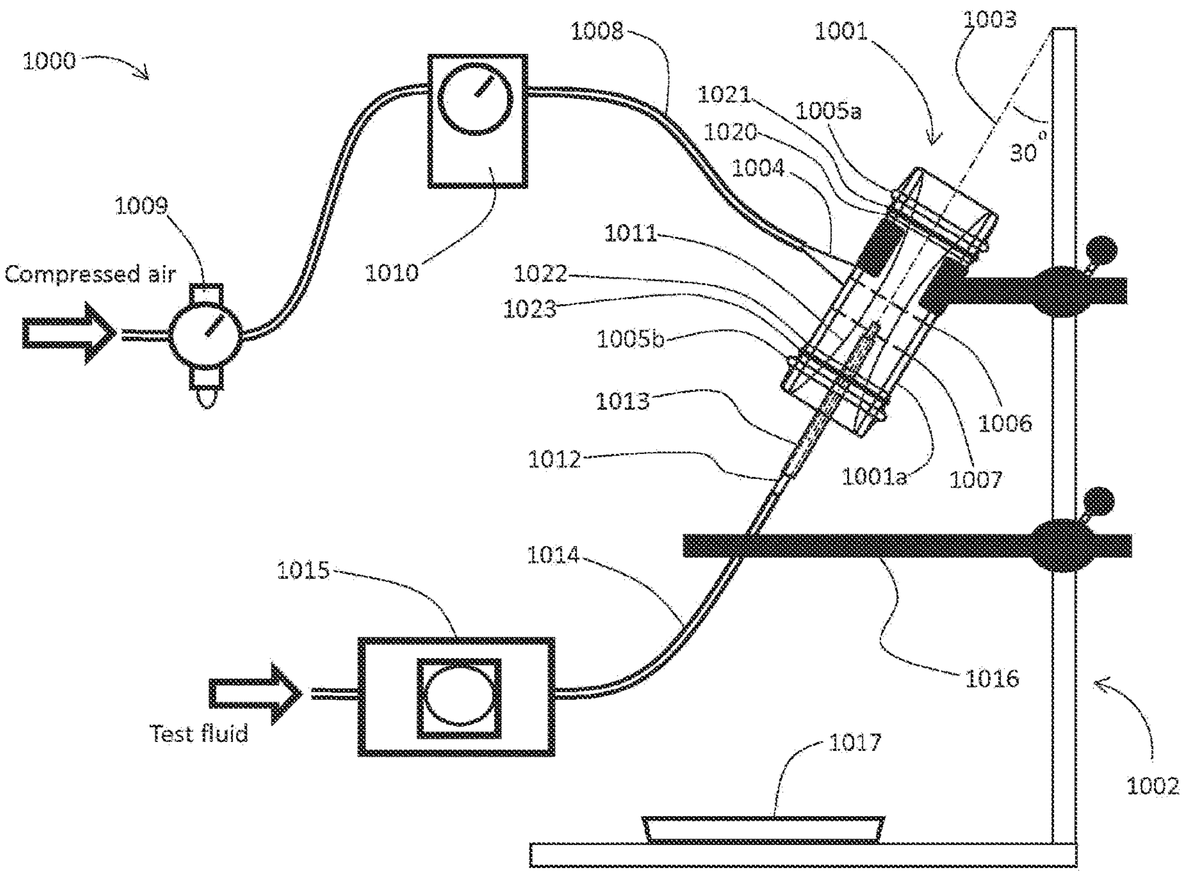
FIGS. 9A and 9B are schematic depictions of a configuration of equipment used in the Wicking Measurement method herein.

The measurement apparatus 1000 is schematically depicted in FIG. 9A. The measurement apparatus 1000 includes a wicking chamber 1001 including a hollow glass tube **1001*a* mounted to a ring stand 1002 in such a way that the longitudinal axis 1003 of the tube 1001*a* lies within a vertical plane and is 30°±2° from a vertical line. The glass tube 1001*a* is open at both ends, and has a 3.3 cm inner diameter, a 3.8 cm outer diameter, and an overall length of 10.5 cm. The glass tube 1001*a* has a ¼ inch hose barb 1004 (that provides fluid communication with the space inside the tube) located at its longitudinal midpoint, extending perpendicularly from the outer surface of the glass tube. Located about 7 mm from each end of the glass tube are circumferential sealing ridges 1005*a*, 1005*b* on the outside of the tube (which may be formed as "marias," also known as "mariahs," as known in glassblowing art), each with a 48.0 mm outer diameter and oriented along a plane perpendicular to the longitudinal axis 1003 of the glass tube. Two lines 1006, 1007 are marked on the glass tube 1001*a*, both oriented along planes perpendicular to the longitudinal axis 1003 of the tube: the Pledget Base Line 1006 is marked at the longitudinal midpoint of the glass tube; the Cannula Position Line 1007 is marked 10.0 mm below the Pledget Base Line 1006. A compressed air source is connected to the hose barb 1004 with flexible tubing 1008. The air pressure is controlled via a pressure regulator 1009 and calibrated manometer 1010 (standardized to ANSI standards). The pressure regulator 1009** is set to 0.5±0.02 psi.

An unlubricated condom 1011 (condom complying with ASTM D3492) is installed inside the glass tube **1001*a* as follows. Unroll the condom 1011 and mark a Positioning Line thereon that is perpendicular to the longitudinal axis of the condom 1011** and located 12.0±0.1 cm from the open end.

Using a glass rod inserted into the condom 1011, push the condom 1011, closed/tip end first, into the lower open end of the glass tube **1001*a*, up through the tube and out the upper open end. Cut off the tip of the closed end of the condom 1011 (no more than about 1 cm from the tip) and discard. Align the Positioning Line marked on the condom with the edge of the open upper end of the glass tube 1001*a*. Now, stretch and pull the newly cut edge 1020 of the condom 1011 radially out, down and over the circumference of the upper edge of the glass tube 1001*a*, and downwardly over and past the upper sealing ridge 1005*a*. Secure the circumferential cut edge of the condom 1011 to the outside of the glass tube 1001*a* below the upper sealing ridge 1005*a*, using a first rubber band 1021. Now, from the bottom, gently pull the condom slightly taut longitudinally, and stretch the circumferential edge 1022 of the original open end of the condom 1011 radially out, up and over the circumference of the lower edge of the glass tube 1001*a* and upwardly past the lower scaling ridge 1005*b*, and secure the circumferential edge of the original open end of the condom 1011 to the outside of the glass tube 1001***a* above the lower sealing ridge 1005*b*, using a second rubber band 1023.

(The references "up", "down", "upper", "lower", and similar terms used in this measurement method description are relative the position of the glass tube when mounted to and held by the ring stand as shown in FIG. 9A. However, the condom may be installed within the glass tube before it is mounted on the ring stand. Similarly, the Pledget Base Line and Cannula Position Line on the glass tube as described above may be marked on the tube before it is mounted on the ring stand.)

The test fluid used (for purposes of providing a fluid having a suitable degree of similarity to human menstrual fluid) is defibrinated sheep's blood, with a packed cell volume between 38%-42% (such as that available from Cleveland Scientific Ltd., Bath, OH, or equivalent) and a viscosity between 6.5-8.0 centistokes. Prior to use in this measurement method, the viscosity of the test fluid is measured using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and the instrument is operated and calibrated as per the manufacturer's instructions. Measurements are taken at 23° C.±1 C.° and at 60 rpm. Results are recorded to the nearest 0.01 centistokes and must be in spec before use.

The test fluid is placed in a 250 mL reservoir with a cover and continuously and moderately stirred to avoid separation. The temperature of the test fluid is maintained at 23° C.±2 C.° during use. The test fluid is supplied from the reservoir to a 15-gauge steel laboratory cannula 1012 (about 10 cm long with a blunt tip at each end with an inner diameter of 1.33-1.41 mm and an outer diameter of 1.82-1.84 mm (such as that available from Cadence Science Inc., 2080 Plainfield Pike, Cranston, RI 02921, or equivalent) and cannula sleeve 1013 (transparent flexible silicone tubing with 3.2 mm inner diameter, 4.8 mm outer diameter, about 7 cm long (such as that available from Cole Parmer, Verner Hills, IL, or equivalent) with peristaltic pump tubing 1014 that has an inner diameter of 1.6mm. The cannula 1012 is inserted through the prepared cannula sleeve 1013 such that there is about 6 mm of the upper/distal tip of the cannula 1012 extending beyond the upper/distal edge of cannula sleeve 1013. (The purpose of the cannula sleeve, of an inner diameter greater than the outer diameter of the cannula, is to provide a pathway for fluid that is not captured and wicked after contacting the wicking member, to flow under gravitational pull down and out of the test chamber, thereby helping reduce chances of pooling of the fluid within the test chamber.) The lower end of the cannula 1012 is inserted into the peristaltic pump tubing 1014. A peristaltic pump 1015 (such as MASTERFLEX®, available from Cole Parmer, Verner Hills, IL, or equivalent) is programmed to deliver 5.0 g±0.25 g of test fluid at 1.0 g/min±0.02 g/min (i.e., over a 5-minute period of operation of the pump). Prior to commencement of the measurement, the peristaltic pump 1015 is calibrated with the test fluid, and the tubing 1014 and cannula 1012 are then primed with test fluid.

A cannula stabilizing bar 1016 is mounted to the ring stand 1002 such that it is about 2 cm below the bottom of the wicking chamber 1001, however, this position can be adjusted as needed. The cannula stabilizing bar 1016 is used to support the peristaltic pump tubing 1014 in order to allow the cannula 1012 to be maintained in a position in which its longitudinal axis is approximately parallel to longitudinal axis 1003 of the glass tube 1001*a* during the measurement.

Tampon measurement samples still in their applicators and wrappers are conditioned at 23° C.±2 C.° and 50±2% relative humidity for at least 2 hours prior to use. Measurement samples are not removed from their wrappers or applicators until immediately prior to use, and must be used within 30 minutes following removal. Clean disposable exam grade, nitrile rubber, powder-free medical gloves must be worn while preparing the measurement samples and during the measurement procedure in order to prevent any contamination from contact with the analyst's hands. Each tampon measurement sample is prepared by first removing the tampon 10 from its applicator in the manner the product is designed to effect ejection of the tampon from the applicator. Cut the withdrawal cord 12 from the tampon 10 at the rear end of the trailing portion 15*b* of the wicking member 15. After cutting away such portion of the withdrawal cord, record the Dry Mass of the tampon measurement sample to the nearest 0.01 g.

Figure 9B:
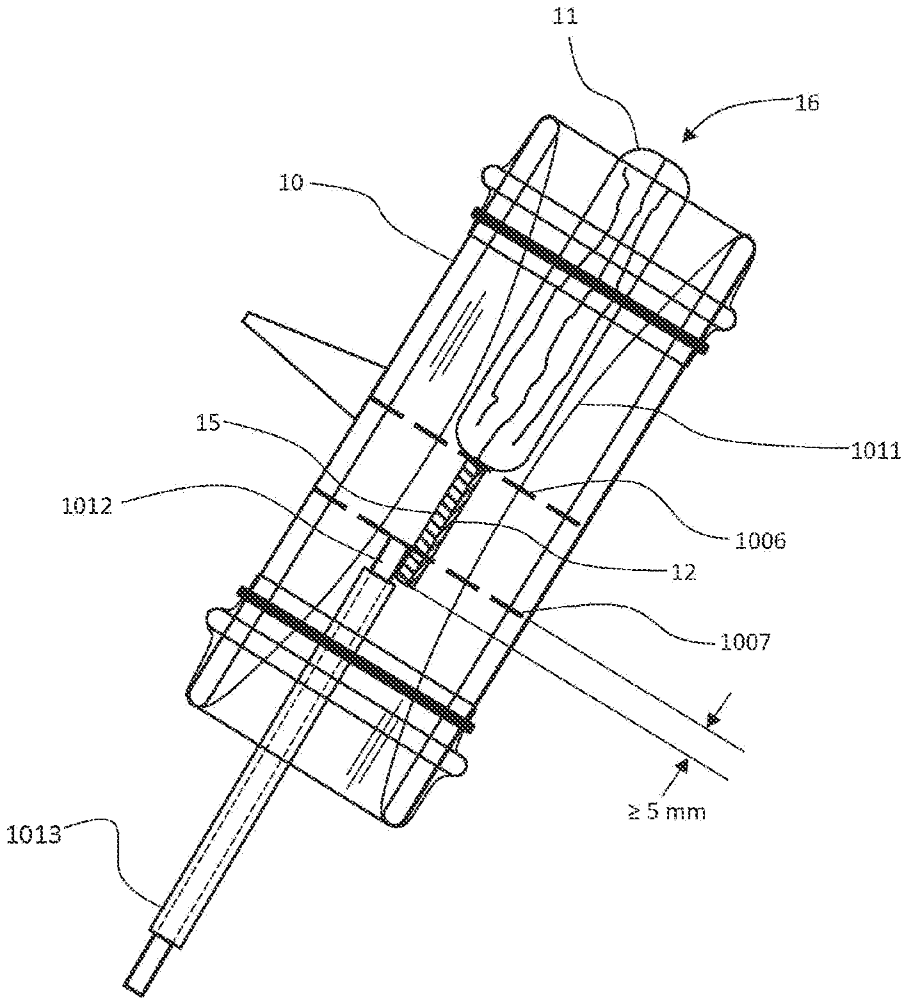

Now referring to FIG. 9B, the tampon measurement sample is placed into the unpressurized wicking chamber 1001 as follows. (A second analyst may be required to assist in manipulating the measurement sample and cannula into position and holding them in position until the measurement chamber is pressurized.) Insert the forward end 16 of the pledget 11 into the bottom of the wicking chamber 1001 and move the sample upward in the chamber to a location at which the rearward end 17 of the pledget 11 is aligned with the Pledget Base Line 1006. Align the longitudinal axis of the pledget and wicking member 15 approximately with the longitudinal axis 1003 of the wicking chamber 1001. If the wicking member 15 and remaining portion of withdrawal cord 12 are not coaxial, rotate the tampon measurement sample about its longitudinal axis within the chamber, to a position in which the trailing portion 15*b* of the wicking member 15 occupies a predominately dorsal (overlying) position relative the remaining portion of the withdrawal cord, and the remaining portion of the withdrawal cord 12 occupies a predominately ventral (underlying) position relative the trailing portion 15*b* of the wicking member. While holding the measurement sample in place inside the wicking chamber 1001 in this position, insert the prepared cannula 1012 with attached cannula sleeve 1013 into the bottom of the wicking chamber 1001 and move it upward within the chamber to a position at which the upward tip of the cannula 1012 is aligned with the Cannula Position Line 1007, and positioned directly over and in contact with the dorsal surface of the wicking member 15, and overlaps it by at least 5 mm. (If the trailing portion 15*b* of wicking member 15 of the particular tampon sample is shorter than 15 mm when in a straightened but substantially relaxed condition so as to provide ≥5 mm overlap, position the cannula tip over the wicking member so that it overlaps the trailing end of the wicking member by ⅓ of the length of the trailing portion 15*b*. If the trailing portion 15*b* of wicking member 15 of the particular tampon sample is shorter than 6 mm when in a straightened but substantially relaxed condition, then the sample cannot be tested according to this method, and does not fall within the contemplation of claims herein that recite a value for Wicking.)

Now, pressurize the wicking chamber 1001 to 0.5±0.02 psi (over ambient air pressure) such that the condom 1011 inflates within the wicking chamber around the measurement sample and cannula 1012 to hold them in place inside the chamber 1001. Ensure that there is still a distance of 6 mm between the tip of the cannula 1012 and the edge of the cannula sleeve 1013. Adjust the position of the cannula stabilizing bar 1016 so that it supports the peristaltic pump tubing 1014 to allow the longitudinal axis of the cannula 1012 to be maintained in a position that is approximately parallel to the longitudinal axis 1003 of the wicking chamber 1001. Adjust as needed to maintain this position throughout the measurement.

Prior to starting of the peristaltic pump, a tray 1017 or other suitable collection means may be placed on the bench-top below the bottom of the cannula sleeve 1013 and wicking chamber 1001 to collect any test fluid that is not wicked/absorbed by the measurement sample and exits the bottom of the test chamber.

Start the peristaltic pump 1015 to deliver 5.0 g±0.25 g of test fluid at 1.0 g/min±0.02 g/min through the cannula 1012. While the test fluid is being delivered, ensure that the tip of the cannula 1012 remains in contact with the trailing portion 15*b* of the wicking member 15 and that there is no pooling of fluid in a crease in the condom 1011 proximate the cannula tip. If pooling of test fluid is observed, move the cannula 1012 slightly further down the trailing portion 15*b* of the wicking member 15. If pooling of test fluid continues, discard the tampon and repeat using a new measurement sample.

After the pump stops, depressurize the wicking chamber 1001 and remove the test sample. Record the Wet Mass of the test sample to the nearest 0.01 g. Calculate the mass of fluid absorbed by the test sample as Wet Mass—Dry Mass and record as Total Uptake to the nearest 0.01 g. The condom 1011 is wiped clean in between test samples and replaced after every 10 samples are tested.

In like fashion, repeat for a total of ten replicate test samples. Calculate the arithmetic mean for Total Uptake measured across all ten replicate test samples and report to the nearest 0.01 g.

In view of the description above, the following non-limiting examples of tampons are contemplated:

1. A tampon, comprising:
   - a pledget, having a forward end and a rearward end, the pledget comprising a discrete first assembly comprising a first fibrous material composition;
   - a withdrawal cord joined to the pledget, and
   - a wicking member disposed in direct contact with the pledget, comprising a discrete second assembly separate and distinct from the first assembly and from the withdrawal cord, the wicking member having a length and being non-coaxially-arranged with respect to the withdrawal cord.

2. The tampon of example 1 wherein the wicking member comprises a second fibrous material composition differing from the first fibrous material composition.

3. The tampon of example 2, wherein the second fibrous material composition differs from the first fibrous material composition in one or more of fiber component composition, density of fiber consolidation, fiber hydrophilicity, or a combination thereof.

4. The tampon of any of the preceding examples wherein the wicking member length includes a trailing portion extending from the rearward end of the pledget, the trailing portion being at least 6 mm long, and the tampon exhibits Wicking of at least 1.2 grams, more preferably at least 1.5 grams, and even more preferably at least 1.8 grams.

5. The tampon of example 4, exhibiting Wicking of no more than 4 grams.

6. A tampon, comprising:
   - a pledget, having a forward end and a rearward end, the pledget comprising a discrete first assembly comprising a first fibrous material composition;
   - a withdrawal cord joined to the pledget, and
   - a wicking member disposed in direct contact with the pledget, comprising a discrete second assembly separate and distinct from the first assembly and from the withdrawal cord, the wicking member having a length including a trailing portion extending from the rearward end of the pledget, and being non-coaxially-arranged with respect to the withdrawal cord;
   - wherein the trailing portion is at least 6 mm long, and the tampon exhibits Wicking of at least 1.2 grams, more preferably at least 1.5 grams, and even more preferably at least 1.8 grams.

7. The tampon of example 6, exhibiting Wicking of no more than 4 grams.

8. The tampon of any of the preceding examples wherein the wicking member and withdrawal cord are joined to each other along at least a portion of the length of the wicking member.

9. The tampon of example 8 wherein a trailing length and trailing end of the wicking member are not joined to the withdrawal cord.

10. The tampon of example 8 wherein a leading length and leading end of the wicking member are not joined to the withdrawal cord.

11. The tampon of any of the preceding examples wherein the withdrawal cord and the wicking member are stitched to each other and stitched to the pledget by a single line of lockstitching.

12. The tampon of example 11 wherein the withdrawal cord and the wicking member are stitched to each other and stitched to the pledget by a single line of lockstitching penetrating the withdrawal cord, wicking member and pledget, the line of lockstitching extending along a majority, preferably substantially the entirety, of a length of the withdrawal cord.

13. The tampon of either of examples 11 or 12 wherein the lockstitching comprises thread material that is inherently hydrophobic, or is treated to be hydrophobic.

14. The tampon of example 13 wherein the thread material comprises polyester.

15. The tampon of any of the preceding examples wherein the withdrawal cord comprises fibrous material that is inherently hydrophobic, or is treated to be hydrophobic.

16. The tampon of any of the preceding examples wherein the wicking member comprises fibrous material that is inherently hydrophilic, or is treated to be hydrophilic.

17. The tampon of any the preceding examples wherein a majority of fibers comprised by the wicking member are predominately oriented in a longitudinal direction.

18. The tampon of any the preceding examples wherein a majority of fibers comprised by the wicking member are predominately oriented in a lateral direction.

19. The tampon of example 16 or 17 wherein the wicking member comprises fibers that are braided or twisted.

20. The tampon of any of the preceding examples wherein fibers comprised by the wicking member are carded.

21. The tampon of example 19 wherein the braided or twisted fibers are continuous fibers.

22. The tampon of example 21 wherein the continuous fibers are tow fibers.

23. The tampon of any of examples 14-22 wherein a majority, and preferably substantially all, of the fibers comprised by the wicking member are not knitted or woven.

24. The tampon of any of the preceding examples wherein a majority of the fibrous material comprised by the wicking member is not cotton fiber, rayon fiber, or a combination thereof.

25. The tampon of any of the preceding examples wherein the pledget comprises material selected from cotton fiber and rayon fiber, and combinations thereof.

26. The tampon of example 25 wherein cotton fiber constitutes a majority of the weight of the pledget.

27. The tampon of example 25 wherein rayon fiber constitutes a majority of the weight of the pledget.

28. The tampon of any of the preceding examples wherein the withdrawal cord comprises cotton.

29. The tampon of example 28 wherein the cotton comprised by the withdrawal cord is hydrophobic.

30. The tampon of any of the preceding examples wherein the withdrawal cord comprises polyester.

31. The tampon of any of the preceding examples wherein the wicking member comprises spun synthetic fibers, preferably fibers spun from polymeric resin, the resin preferably comprising polypropylene.

32. The tampon of any of the preceding examples wherein material comprised by the wicking member is imparted with a second color that visibly contrasts with a first color of the pledget.

33. The tampon of any of the preceding examples wherein the first assembly of absorbent material comprises cotton and/or rayon fiber disposed within a wrapper, or disposed between sections of fabric.

34. The tampon of example 33 wherein the wrapper or sections of fabric comprise polypropylene and/or polyethylene.

35. An array of respective packaged tampon products, comprising a first package and a second package, the first package comprising first tampons according to any of the preceding examples and the second package comprising second tampons according to any of the preceding examples, wherein wicking members of the first tampons differ from wicking members of the second tampons in one or more of physical structure, material(s) composition(s), size, wicking performance and imparted color.

36. The array of example 35 wherein pledgets of the first tampons differ from pledgets the second tampons in one or more of physical structure, material(s) composition(s), size and absorption capacity.

37. The array of either of examples 35 or 36 wherein the first package and the second package each includes associated material comprising imprinted information in one or more of graphic, pictorial and verbal form, signaling the differences in the respective pledgets and/or the respective wicking members.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon, comprising:

a pledget, having a forward end and a rearward end, the pledget comprising a discrete first assembly comprising a first fibrous material composition;

a withdrawal cord joined to the pledget, and a wicking member having a leading portion and a trailing portion, wherein the wicking member is disposed in direct contact with the pledget, wherein the leading portion of the wicking member is disposed nearer to the forward end of the pledget than is the trailing portion of the wicking member, wherein the leading portion of the wicking member is disposed longitudinally inboard of the forward end of the pledget and the trailing portion of the wicking member extends from and beyond the rearward end of the pledget, wherein the wicking member comprises a discrete second assembly separate and distinct from the first assembly and from the withdrawal cord, the wicking member having a length and being non-coaxially-arranged with respect to the withdrawal cord, and wherein the wicking member is disposed between the first assembly and the withdrawal cord.

2. The tampon of claim 1, wherein the wicking member comprises a second fibrous material composition differing from the first fibrous material composition.

3. The tampon of claim 2, wherein the second fibrous material composition differs from the first fibrous material composition in one or more of fiber component composition, density of fiber consolidation, fiber hydrophilicity, or a combination thereof.

4. The tampon of claim 1, wherein the tampon exhibits Wicking of no more than 4 grams, wherein the Wicking is measured using the Wicking Measurement Method and wherein the Wicking indicates an ability of the wicking member to capture and wick fluid through the wicking member up to the pledget.

5. The tampon of claim 1, wherein the wicking member and withdrawal cord are joined to each other along at least a portion of the length of the wicking member.

6. The tampon of claim 5, wherein a trailing length and trailing end of the wicking member are not joined to the withdrawal cord.

7. The tampon of claim 1, wherein the withdrawal cord and the wicking member are stitched to each other and stitched to the pledget by a single line of lockstitching.

8. The tampon of claim 7, wherein the lockstitching comprises thread material that is inherently hydrophobic, or is treated to be hydrophobic.

9. The tampon of claim 1, wherein a majority of the fibrous material comprised by the wicking member is not cotton fiber, rayon fiber, or a combination thereof.

10. The tampon of claim 9, wherein the wicking member comprises spun synthetic fibers.

11. The tampon of claim 1, wherein material comprised by the wicking member is imparted with a second color that visibly contrasts with a first color of the pledget.

12. An array of respective packaged tampon products, comprising a first package and a second package, the first package comprising first tampons according to claim 1 and the second package comprising second tampons according to claim 1, wherein wicking members of the first tampons differ from wicking members of the second tampons in one or more of physical structure, material(s) composition(s), size, wicking performance, and imparted color.

13. The array of claim 12, wherein pledgets of the first tampons differ from pledgets of the second tampons in one or more of physical structure, material(s) composition(s), size, and absorption capacity.

14. The tampon of claim 1, further comprising a hydrophilic wrapper substantially covering the pledget.

15. The tampon of claim 1, wherein the withdrawal cord is joined substantially along an entire length of the pledget from the forward end to the rearward end.

16. The tampon of claim 1, wherein the wicking member is not intermingled with the withdrawal cord and is non-coaxially arranged with respect to the withdrawal cord such that the wicking member and the withdrawal cord are arranged in contact with each other along a substantially parallel non-coaxial configuration where longitudinal axes of the wicking member and the withdrawal cord are parallel and not the same.

17. The tampon of claim 1, wherein the trailing portion of the wicking member comprises a free end that is not stitched or affixed to the withdrawal cord.

18. A tampon, comprising:

a pledget, having a forward end and a rearward end, the pledget comprising a discrete first assembly comprising a first fibrous material composition;

a withdrawal cord joined to the pledget, and a wicking member having a leading portion and a trailing portion, wherein the wicking member is disposed in direct contact with the pledget, wherein the leading portion of the wicking member is disposed nearer to the forward end of the pledget than is the trailing portion of the wicking member, wherein the leading portion of the wicking member is disposed between the forward end and the rearward end of the pledget, wherein the leading portion of the wicking member is disposed longitudinally inboard of the forward end of the pledget, wherein the wicking member comprises a discrete second assembly separate and distinct from the first assembly and from the withdrawal cord, the wicking member being non-coaxially-arranged with respect to the withdrawal cord such that the wicking member and the withdrawal cord are arranged in contact with each other along a substantially parallel non-coaxial configuration where longitudinal axes of the wicking member and the withdrawal cord are parallel and not the same; and wherein the trailing portion of the wicking member extends from and beyond the rearward end of the pledget a length of at least 6 mm, and the tampon exhibits Wicking of at least 1.5 grams, wherein the Wicking is measured using the Wicking Measurement Method and wherein the Wicking indicates an ability of the wicking member to capture and wick fluid through the wicking member up to the pledget.

19. The tampon of claim 18, wherein the tampon exhibits Wicking of no more than 4grams.

20. The tampon of claim 18, wherein the wicking member comprises a second fibrous material composition differing from the first fibrous material composition.

21. The tampon of claim 20, wherein the second fibrous material composition differs from the first fibrous material composition in one or more of fiber component composition, density of fiber consolidation, fiber hydrophilicity, or a combination thereof.

22. The tampon of claim 18, wherein a majority of the fibrous material comprised by the wicking member is not cotton fiber, rayon fiber, or a combination thereof.

23. The tampon of claim 18, wherein the wicking member comprises spun synthetic fibers.

* * * * *